(12) United States Patent
Okada

(10) Patent No.: US 9,649,015 B2
(45) Date of Patent: May 16, 2017

(54) TREATMENT TOOL FOR ENDOSCOPE

(71) Applicant: OLYMPUS CORPORATION, Tokyo (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/883,077

(22) Filed: Oct. 14, 2015

(65) Prior Publication Data

US 2016/0029875 A1 Feb. 4, 2016

Related U.S. Application Data

(63) Continuation of application No. PCT/JP2014/062693, filed on May 13, 2014.

(30) Foreign Application Priority Data

Jun. 11, 2013 (JP) .................. 2013-122635

(51) Int. Cl.
*A61B 1/00* (2006.01)
*A61B 17/00* (2006.01)
(Continued)

(52) U.S. Cl.
CPC ........ *A61B 1/00087* (2013.01); *A61B 1/0014* (2013.01); *A61B 1/00101* (2013.01);
(Continued)

(58) Field of Classification Search
USPC ......... 600/104, 106–107, 121–125, 127, 129
See application file for complete search history.

(56) References Cited

U.S. PATENT DOCUMENTS 4,401,123 A * 8/1983 Baba .................... A61B 1/0051
600/101
4,763,662 A 8/1988 Yokoi
(Continued)

FOREIGN PATENT DOCUMENTS

JP S61-280849 A 12/1986
JP 2004-261372 A 9/2004
(Continued)

OTHER PUBLICATIONS

Jun. 24, 2014 Search Report issued in International Patent Application No. PCT/JP2014/062693.
(Continued)

*Primary Examiner* — Matthew J Kasztejna
(74) *Attorney, Agent, or Firm* — Oliff PLC

(57) ABSTRACT

A treatment tool for an endoscope includes: a distal end member attached to a distal end of an endoscope; a treatment part; a tube that is arranged in an axis direction of the endoscope and has a lumen formed therein; an insertion part that is inserted into the lumen and has a distal end to which the treatment part is fixed; a connecting member that connects the tube and the distal end member; a first pivot that couples the connecting member and the tube; and a second pivot that couples the connecting member and the distal end member. The second pivot is provided at a position at which the connecting member is capable of rotating such that the first pivot is moved from a position at a proximal end side relative to the second pivot to a position at a distal end side.

5 Claims, 21 Drawing Sheets

(51) Int. Cl.
  *A61B 17/29* (2006.01)
  *A61B 18/14* (2006.01)
(52) U.S. Cl.
  CPC ....... *A61B 1/00098* (2013.01); *A61B 18/1442* (2013.01); *A61B 2017/00269* (2013.01); *A61B 2017/00296* (2013.01); *A61B 2017/2905* (2013.01); *A61B 2017/2906* (2013.01)

(56) References Cited

U.S. PATENT DOCUMENTS

| | | | | |
|---|---|---|---|---|
| 7,566,300 B2* | 7/2009 | Devierre | A61B 1/00087 | 600/104 |
| 7,575,548 B2* | 8/2009 | Takemoto | A61B 1/00087 | 600/104 |
| 8,277,373 B2* | 10/2012 | Maahs | A61B 1/0008 | 600/104 |
| 2003/0040657 A1 | 2/2003 | Yamaya et al. | | |
| 2003/0176766 A1 | 9/2003 | Long et al. | | |
| 2004/0225305 A1* | 11/2004 | Ewers | A61B 1/00135 | 606/153 |
| 2005/0234296 A1* | 10/2005 | Saadat | A61B 1/0008 | 600/129 |
| 2005/0234297 A1 | 10/2005 | Devierre et al. | | |
| 2008/0177135 A1* | 7/2008 | Muyari | A61B 1/00087 | 600/104 |
| 2008/0249354 A1 | 10/2008 | Muyari et al. | | |
| 2008/0269562 A1* | 10/2008 | Marescaux | A61B 1/00087 | 600/142 |
| 2010/0036198 A1* | 2/2010 | Tacchino | A61B 1/0014 | 600/106 |
| 2010/0113873 A1 | 5/2010 | Suzuki et al. | | |

FOREIGN PATENT DOCUMENTS

| | | |
|---|---|---|
| JP | 2008-253597 A | 10/2008 |
| JP | 2010022568 A | 2/2010 |
| JP | 2011-245180 A | 12/2011 |
| JP | 4847354 B2 | 12/2011 |
| JP | 2012-024597 A | 2/2012 |
| JP | 4980777 B2 | 7/2012 |
| WO | 2009/117696 A1 | 9/2009 |
| WO | 2010/053118 A1 | 5/2010 |

OTHER PUBLICATIONS

Feb. 3, 2017 extended European Search Report issued in European Application No. 14811576.9.

* cited by examiner

TREATMENT TOOL FOR ENDOSCOPE

This application is a continuation application based on PCT Patent Application No. PCT/JP2014/062693, filed May 13, 2014, whose priority is claimed on Japanese Patent Application No. 2013-122635 filed on Jun. 11, 2013. The contents of both the PCT Patent Application and the Japanese Patent Application are incorporated herein by reference.

BACKGROUND OF THE INVENTION

Field of the Invention

The present invention relates to a treatment tool for an endoscope used together with an endoscope.

Description of Related Art

In the related art, as general methods of treating gastrointestinal tract lesions, endoscopic mucosal resection (EMR) in which lesion parts are resected using an endoscope is performed. In particular, endoscopic submucosal dissection (hereinafter referred to as "ESD") is a method in which mucosae in the vicinity of lesion parts are cut and then submucosae are dissected to resect the lesion parts, which is known as reliable endoscopic therapy through which lesion parts could be resected entirely.

When such ESD is performed, a normal saline or the like is injected into normal mucosae in the vicinity of lesion parts using a needle and the lesion parts are lifted. In this state, a high frequency treatment tool such as a high frequency knife or a snare is used to resect a boundary between lesion parts and normal mucosae (for example, refer to Japanese Unexamined Patent Application, First Publication No. 2004-261372). In this case, in order to sufficiently lift the lesion parts up to a position so that a resection part of a boundary between lesion parts and normal tissues is sufficiently ensured, or in order to capture the resection part when the lesion parts have a flat shape, a transparent cap mounted on a distal end of the endoscope is inserted below mucosae to lift the mucosae, and the high frequency treatment tool proceeds with incision of submucosae.

However, since a distal end diameter of the transparent cap is greater than a distal end diameter of the endoscope, it is difficult to insert the endoscope into a fine incision wound and open the incision wound. In addition, even if a distal end cap is inserted into the incision wound, mucosae may slide off the distal end cap when the endoscope is operated to perform incision or dissection.

In order to prevent such problems, a treatment tool for an endoscope including a treatment part capable of capturing biological tissues such as mucosae is proposed (for example, refer to Japanese Patent No. 4980777 and Japanese Patent No. 4847354). According to the treatment tool for an endoscope, when a distal end cap is inserted below mucosae in order to cut submucosae, the treatment part can lift mucosae up, and submucosae can be viewed by the endoscope in a front view.

Moreover, a treatment tool for an endoscope in which a sheath to which a treatment part is connected is advanced or retracted in a central axis direction and the sheath is raised to separate a distal end of the treatment part from a distal end cap is disclosed (for example, refer to FIGS. 9 and 10 of Japanese Unexamined Patent Application, First Publication No. 2012-24597). All of these tools ensure a field of view of a portion to be cut by lifting mucosae up and pulling them toward the endoscope using the treatment part.

SUMMARY OF THE INVENTION

According to a first aspect of the present invention, a treatment tool for an endoscope comprising: a distal end member that is attached to a distal end of an endoscope and has a cylindrical shape; a treatment part that performs treatment on biological tissues; an insertion part that has a distal end to which the treatment part is fixed; a tube that is arranged substantially parallel to an axis of the distal end member, arranged at a side surface of the distal end member, and configured to hold the insertion part; and a connecting member that includes a first pivot which has a first central axis extending in a direction intersecting an axis of the tube and which is coupled with the tube such that the first pivot is capable of rotating about the first central axis relative to the tube, and a second pivot which has a second central axis substantially parallel to the first central axis of the first pivot and which is coupled with the distal end member such that the second pivot is capable of rotating about the second central axis relative to the distal end member, the connecting member being configured to connect the first pivot and the second pivot. The second pivot is coupled with the distal end member such that the first pivot is capable of rotating about the second central axis of the second pivot. The tube is coupled with the first pivot such that the tube is capable of moving relative to the first pivot in a direction in which the first central axis of the first pivot extends.

According to a second aspect of the present invention, in the treatment tool according to the first aspect of the present invention, the tube may be configured to hold the insertion part such that the insertion part is capable of advancing and retracting.

According to a third aspect of the present invention, in the treatment tool according to the first aspect of the present invention, the distal end member may include: a mounting member configured to be detachably attached to the distal end of the endoscope; and a cap positioned at a distal end side of the mounting member.

According to a fourth aspect of the present invention, in the treatment tool according to the first aspect of the present invention, the distal end member may be provided with a coating part into which the tube is inserted in an advanceable and retractable manner.

According to a fifth aspect of the present invention, in the treatment tool according to the first aspect of the present invention, the tube and the treatment part may be configured to be prevented from rotating relative to each other.

DETAILED DESCRIPTION OF THE INVENTION

Figure 1:
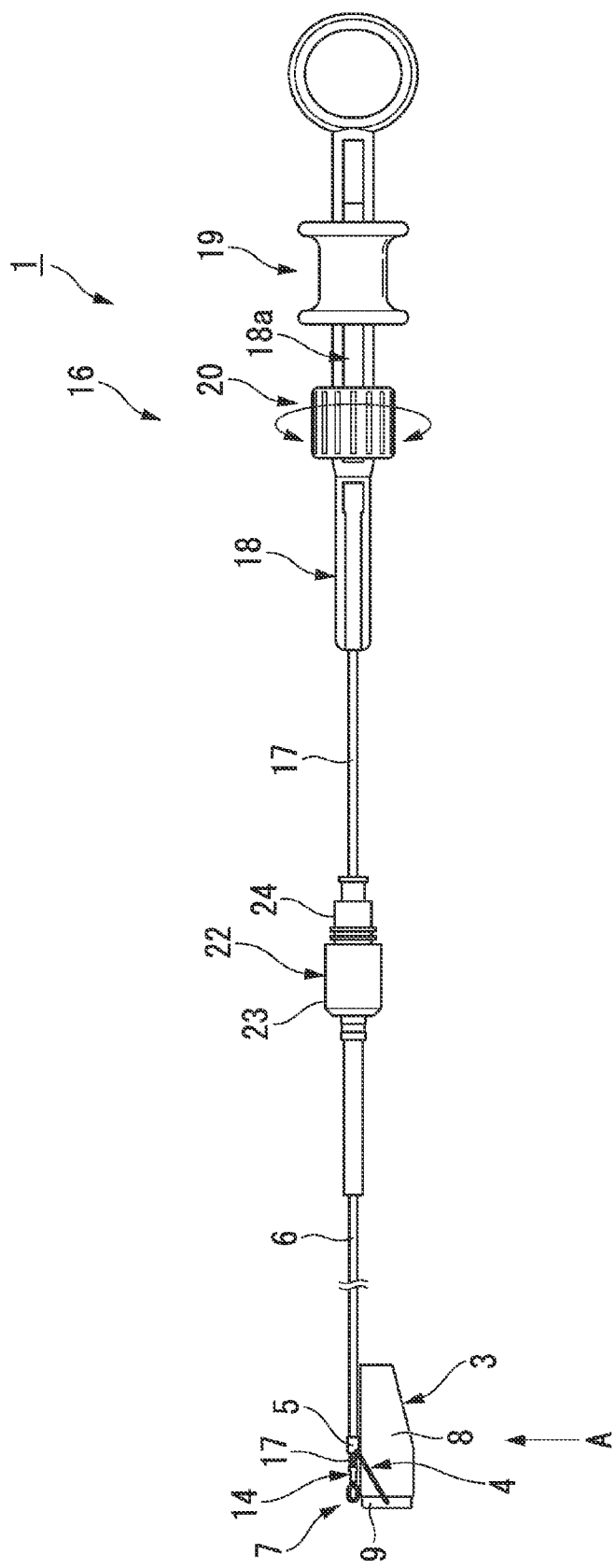
FIG. 1 is a front view schematically showing a treatment tool for an endoscope according to a first embodiment of the present invention.

Hereinafter, embodiments of the present invention will be described with reference to the accompanying drawings. In all diagrams, the same or corresponding members are denoted by the same reference numerals even when embodiments are different, and common descriptions will be omitted.

First Embodiment

Figure 2:
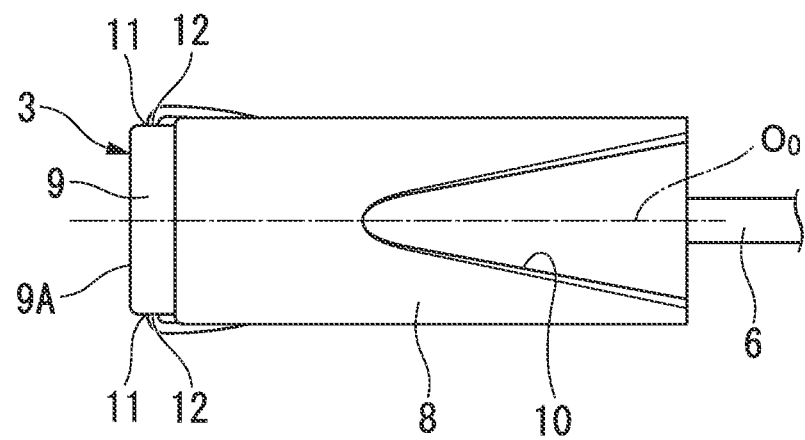
FIG. 2 is a view seen from the arrow A in FIG. 1.
Figure 3:
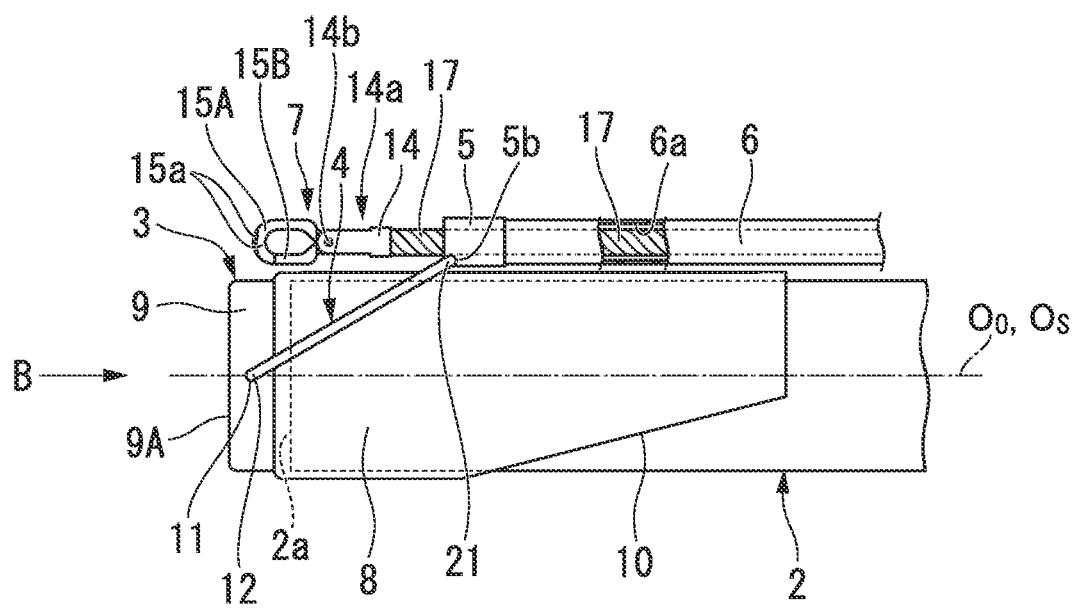
FIG. 3 is a front view schematically showing a state in which a distal end member and a treatment part of the treatment tool for an endoscope according to the first embodiment of the present invention are mounted on an endoscope.
Figure 4:
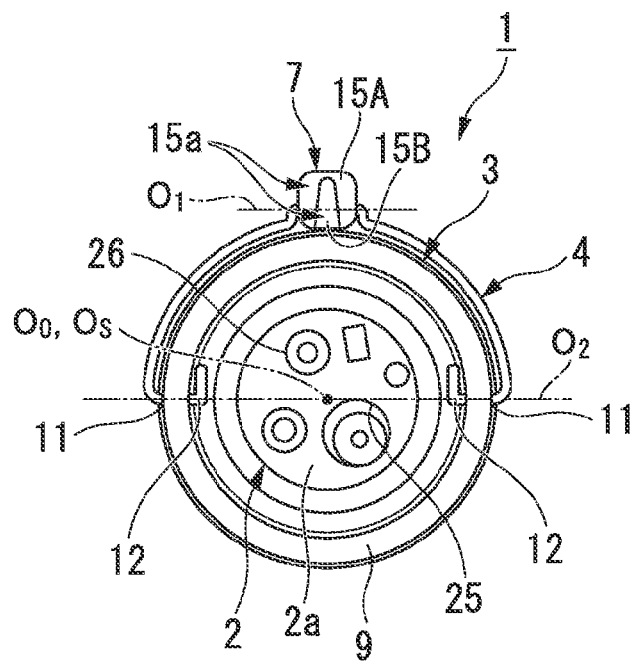
FIG. 4 is a view seen from the arrow B in FIG. 3.
Figure 5:
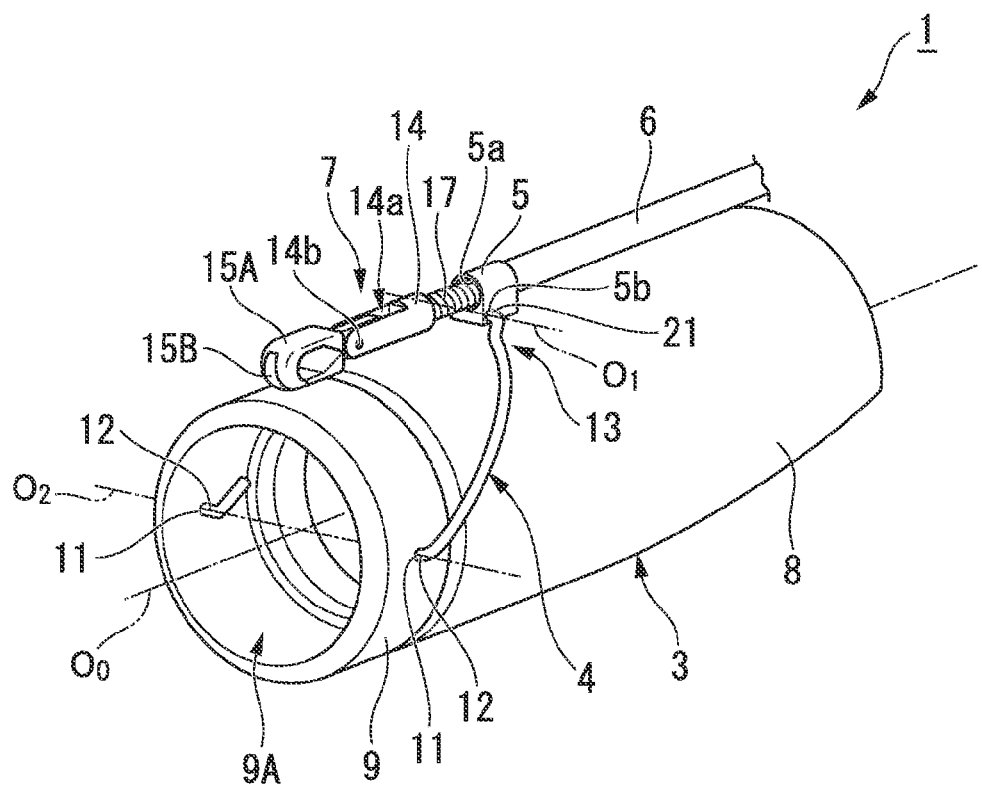
FIG. 5 is a perspective view schematically showing a distal end member and a treatment part of the treatment tool for an endoscope according to the first embodiment of the present invention.

The treatment tool for an endoscope according to the first embodiment of the present invention will be described. FIG. 1 is a front view schematically showing the treatment tool for an endoscope according to the first embodiment of the present invention. FIG. 2 is a view seen from the arrow A in FIG. 1. FIG. 3 is a front view schematically showing a state in which a distal end member and a treatment part of the treatment tool for an endoscope according to the first embodiment of the present invention are mounted on an endoscope. FIG. 4 is a view seen from the arrow B in FIG. 3. FIG. 5 is a perspective view schematically showing a distal end member and a treatment part of the treatment tool for an endoscope according to the first embodiment of the present invention.

As shown in FIG. 1, a treatment tool 1 for an endoscope includes a distal end member 3, a moving member 5, a tube 6, a sheath 17 (insertion part), and a capturing part 7 (treatment part). The distal end member 3 is mounted on a distal end of the endoscope (not shown). The moving member 5 is formed in a tube shape and coupled to the distal end member 3 through a connecting member 4. A lumen 6a is formed to penetrate the tube 6 in a longitudinal direction, and a distal end of the tube 6 is fixed to the moving member 5. The sheath 17 is inserted into the moving member 5 and the lumen 6a of the tube 6. The capturing part 7 is supported through a support member 14 at a distal end of the sheath 17 exposed from a distal end of the moving member 5 and holds biological tissues.

As shown in FIGS. 2 and 3, the distal end member 3 includes a mounting part 8 (mounting member) and a cap 9, and is a tubular member as a whole. The mounting part 8 is formed in a substantially cylindrical shape, and mounted on a distal end of an endoscope 2 (refer to FIG. 3). The cap 9 is formed in a tube shape and integrally provided in the mounting part 8 at a distal end side of the mounting part 8.

The mounting part 8 is provided such that a slit 10 is parallel in a longitudinal direction (a horizontal direction shown in FIGS. 2 and 3) from a proximal end side (the right side of FIGS. 2 and 3) of a cylindrical part and is made of a soft material. Therefore, the mounting part 8 is easy to mount on the endoscope 2. The cap 9 has a cylindrical shape and is made of a rigid and transparent material. A distal end opening 9A of the cap 9 is arranged at a distal side relative to a distal end surface of the endoscope 2, and forms a substantially parallel opening on the distal end surface of the endoscope 2.

As shown in FIGS. 4 and 5, the connecting member 4 is formed by shaping a rigid wire material, and both end parts of the wire material are inserted into a pair of holes 11 formed on one diameter of the cap 9. The pair of holes 11 are arranged on a circumference of the distal end member 3 to be shifted about 90° from a position in which the slit 10 of the mounting part 8 is formed. In the present embodiment, as one example, an axis $O_2$ along which the pair of holes 11 are aligned is perpendicular to a central axis $O_0$ of the distal end member 3. Both end parts of the connecting member 4 are inserted into the pair of holes 11 one by one from the outside to the inside, folded back into the cap 9, and stop so as not to escape. In the connecting member 4, a part inserted into the hole 11 becomes a second pivot 12 when an operation to be described below is performed. The second pivots 12 are inserted in parallel to the axis $O_2$ of the holes 11 one by one, and the second pivots 12 are arranged on the same axis. In this manner, since the second pivot 12 does not penetrate the entire distal end member 3, a field of view of the endoscope 2 and an operation of a treatment tool that passes through a working channel are not interfered with. In such a configuration, the connecting member 4 is rotatably connected to the cap 9 of the distal end member 3 through the holes 11.

The connecting member 4 is drawn externally from each of the pair of holes 11 in the cap 9, bent to follow an outer shape of the distal end member 3, extends toward the moving member 5, and penetrates through the moving member 5 from a side such that an inside of the moving member 5 has a gap into which the sheath 17 is inserted so as to be capable of advancing and retracting. Therefore, parts 13 of the connecting member 4 in the vicinity of the moving member 5 are bent to sandwich the moving member 5, and a linear shaft part is formed therebetween. Also, the connecting member 4 is curved to follow an outer shape of the distal end member 3 until it reaches the parts 13 from the cap 9 at a side of the moving member 5 or may be bent at one or more locations on the way.

As shown in FIG. 5, in the present embodiment, the moving member 5 includes an opening part 5a and a through-hole 5b. The opening part 5a communicates with the tube 6 so as to insert the sheath 17 thereinto. The connecting member 4 is inserted into the through-hole 5b in a position of the mounting part 8 side relative to the opening part 5a along an axis $O_1$ that is parallel to the axis $O_2$. The moving member 5 is rotatably supported using the shaft part of the connecting member 4 that penetrates through the through-hole 5b as a rotation shaft. Accordingly, the tube 6 fixed to the moving member 5 is also rotatably supported with respect to the shaft part of the connecting member 4. In such a configuration, the shaft part of the connecting member 4 that penetrates through the through-hole 5b forms a first pivot 21 that pivotally couples the connecting member 4 and the tube 6. The first pivot 21 is arranged in parallel to the second pivot 12 and arranged at a position to be shifted about 90° from each of the pair of second pivots 12 using the central axis $O_0$ of the distal end member 3 as a center.

The tube 6 has flexibility and includes a distal end part fixed to the moving member 5. An arrangement position of the tube 6 is a position shifted 90° in a circumferential direction of the distal end member 3 from a position that is a side of the mounting part 8 at a substantially opposite side of the slit 10 and in which each of the pair of holes 11 supporting the connecting member 4 is formed.

The sheath 17 is formed of a tubular member that is longer than the tube 6 and has flexibility, and is inserted into the lumen 6a of the tube 6 and arranged so as to be capable of advancing and retracting along the lumen 6a. Both end parts of the sheath 17 are exposed from the tube 6. In the present embodiment, as one example, as the sheath 17, a coil sheath having flexibility due to densely wound wires is used. The capturing part 7 is fixed to the distal end part of the sheath 17 through the support member 14. An operation wire (not shown) configured to operate the capturing part 7 is inserted into the sheath 17.

As shown in FIG. 1, a second lock mechanism 22 configured to switch disengagement between the tube 6 and the sheath 17 is provided at a proximal end part of the tube 6. The second lock mechanism 22 includes a base member 23 fixed to the tube 6 and an engaging member 24 that can be disengaged from the base member 23. The engaging member 24 is provided so as to approach or separate from the sheath 17 at an outer circumference side of the sheath 17. When the engaging member 24 is engaged with the base member 23, the engaging member 24 comes in close contact with an outer circumference of the sheath 17, and a position of the sheath 17 is fixed to the engaging member 24. In this case, the sheath 17 has a fixed relative position with respect to the tube 6 fixed to the base member 23 engaged with the engaging member 24. Therefore, relative rotation and advancing and retraction with respect to the tube 6 are disabled. That is, the second lock mechanism 22 is locked and a position of the sheath 17 is fixed. When engagement with the base member 23 of the engaging member 24 is released and the engaging member 24 is detached from the base member 23, since the engaging member 24 is separated from the sheath 17, it is possible to rotate and advance and retract the sheath 17 with respect to the tube 6. That is, the second lock mechanism 22 is unlocked and the sheath 17 is movable.

As shown in FIGS. 3 to 5, in the present embodiment, the capturing part 7 includes a pair of forceps members 15A and 15B which have a grasping part 15a configured to grasp biological tissues at a distal end side. The forceps members 15A and 15B, whose proximal end sides are inserted into a slit 14a of the support member 14, are supported such that opening and closing operations are possible by a rotation shaft 14b provided at the slit 14a. In addition, the operation wire (not shown) inserted into the sheath 17 is coupled to proximal end parts of the forceps members 15A and 15B. This operation wire is coupled to an operating part 16 (refer to FIG. 1) provided at a proximal end part of the sheath 17.

As shown in FIG. 1, the operating part 16 includes an operating part main body 18, a slider 19, and a first lock mechanism 20. The slider 19 is arranged so as to advance and retract with respect to a slit 18a provided in a longitudinal direction of the operating part main body 18. The first lock mechanism 20 fixes a movement position of the slider 19. A proximal end of the sheath 17 is connected to the operating part main body 18. A proximal end of the operation wire (not shown) is connected to the slider 19. The first lock mechanism 20 is arranged at a position at a distal end side relative to the slider 19 in a movable range of the slider 19. The first lock mechanism 20 is provided to be movable along the slit 18a of the operating part main body 18. In addition, the first lock mechanism 20 has a mechanism in which, when rotation is performed in a direction indicated by the arrow of FIG. 1, the position of the slider 19 can be fixed in that position. An exemplary example of such a mechanism is, for example, a mechanism in which a clamping member clamping and preventing a slide member (not shown) from being moved is rotatably provided in an outer circumference of the slide member that is linked with the slider 19 and movable along the slit 18a.

As shown in FIGS. 3 and 4, in the treatment tool 1 for an endoscope having such a configuration, the mounting part 8 is mounted on a distal end part of the endoscope 2 and fixed to the endoscope 2. In this case, the central axis $O_O$ of the distal end member 3 is the same as a central axis $O_S$ of the endoscope 2. In FIG. 3, while only the distal end part of the endoscope 2 formed from a rigid part is shown, a curved part of the endoscope 2 is provided at a proximal end side. In such a mounting state, the tube 6 is arranged in an axis direction of the endoscope 2. In this state, as will be described below, when the operating part 16 is advanced or retracted, the tube 6 can be advanced or retracted in the axis direction of the endoscope 2.

A configuration of the endoscope 2 is not particularly limited. Hereinafter, as one example, as shown in FIG. 4, the endoscope 2 including a working channel 25 and an observation device 26 will be described. The working channel 25 is a lumen provided in the endoscope 2 such that an appropriate treatment tool used for treatment is inserted into the lumen and is advanced and retracted from a distal end surface 2a. The observation device 26 is a device part acquiring a picture in front of the distal end surface 2a. In the distal end surface 2a, a light receiving window is provided at a position adjacent to an opening of the working channel 25. The picture acquired by the observation device 26 can be displayed on a monitor or the like through a cable (not shown).

Figure 6:
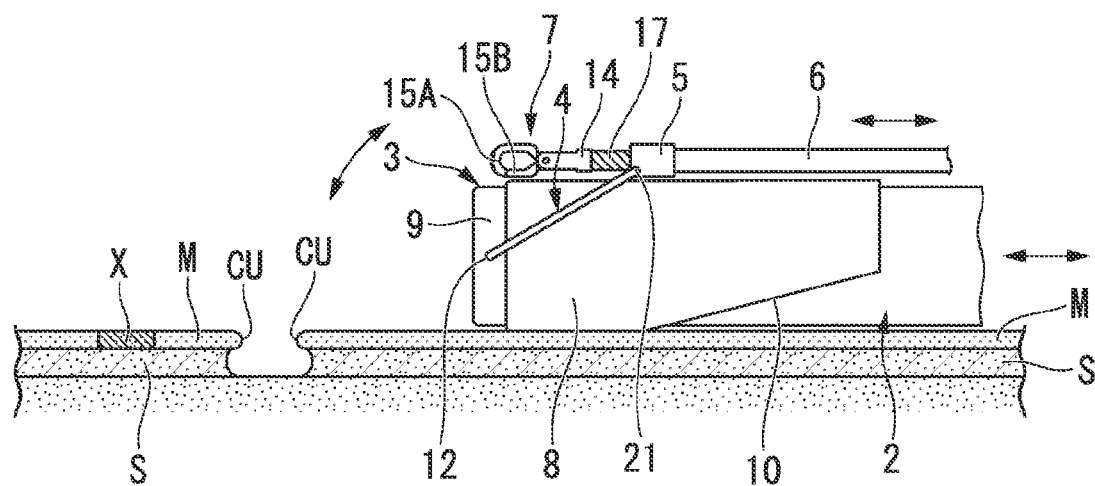
FIG. 6 is an explanatory diagram showing an operation of the treatment tool for an endoscope according to the first embodiment of the present invention.
Figure 7:
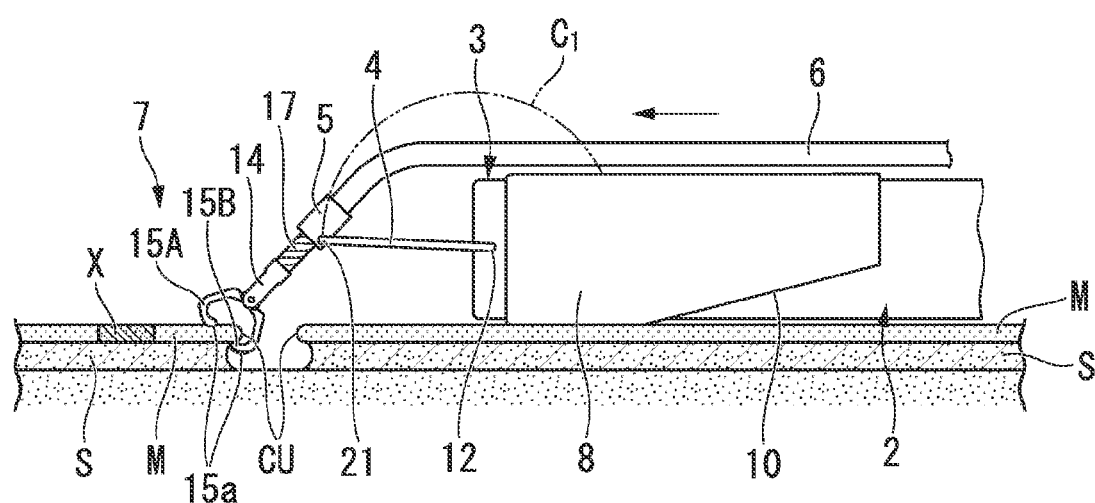
FIG. 7 is an explanatory diagram showing an operation conducted after the operation shown in FIG. 6.
Figure 8:
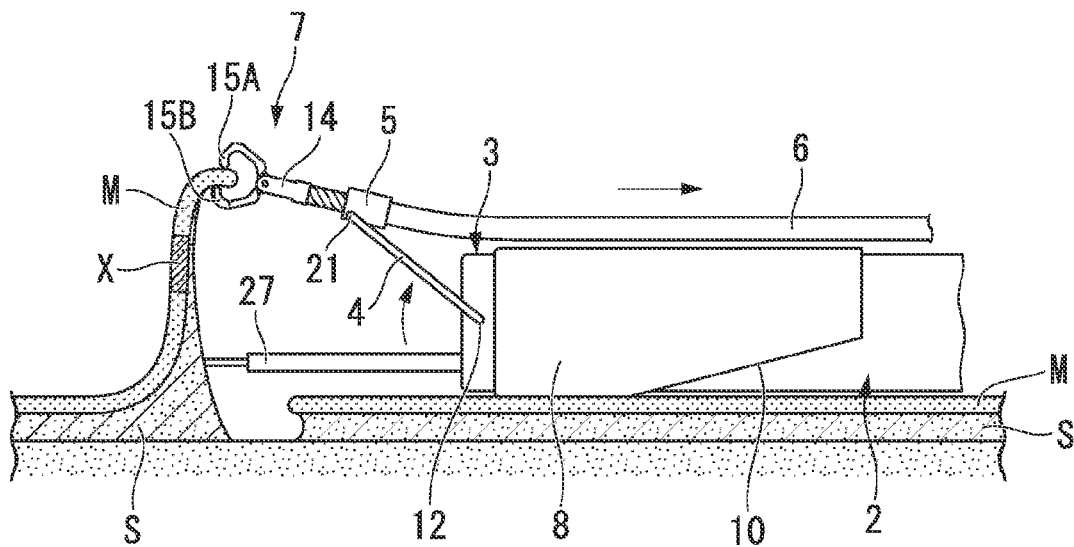
FIG. 8 is an explanatory diagram showing an operation conducted after the operation shown in FIG. 7.
Figure 9:
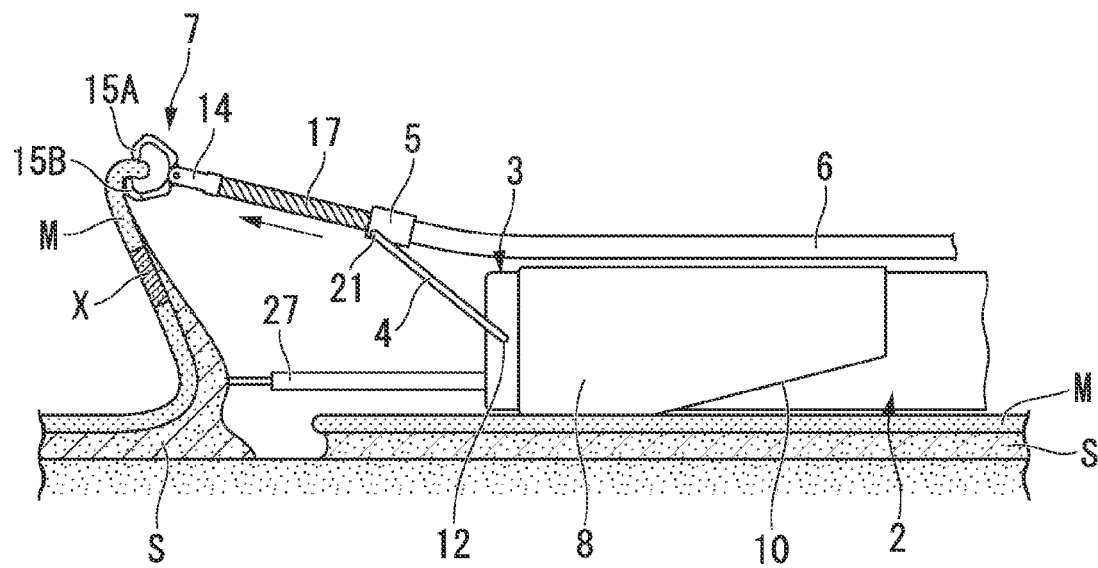
FIG. 9 is an explanatory diagram showing an operation conducted after the operation shown in FIG. 8.

Next, as an operation of the treatment tool 1 for an endoscope according to the present embodiment, an example in which an ESD procedure is performed using the treatment tool 1 for an endoscope will be described. FIG. 6 is an explanatory diagram showing an operation of the treatment tool for an endoscope according to the first embodiment of the present invention. FIG. 7 is an explanatory diagram showing an operation conducted after the operation shown in FIG. 6. FIG. 8 is an explanatory diagram showing an operation conducted after the operation shown in FIG. 7. FIG. 9 is an explanatory diagram showing an operation conducted after the operation shown in FIG. 8.

First, as shown in FIGS. 3 and 4, the mounting part 8 of the treatment tool 1 for an endoscope is mounted on a distal end part of the endoscope 2. In this case, a mounting position of the mounting part 8 is adjusted in a circumferential direction of the endoscope 2. Therefore, as shown in FIG. 4, a position of the capturing part 7 is adjusted such that the capturing part 7 has a position that is separated from the working channel 25 of the endoscope 2. For example, a positional relation is arranged such that the observation device 26 is arranged between the working channel 25 and the capturing part 7. In the treatment tool 1 for an endoscope in this state, when the sheath 17 is advanced or retracted with respect to the tube 6, it is possible to change a position in the axis direction of the endoscope 2 of the capturing part 7. In addition, when the tube 6 is advanced or retracted in the axis direction of the endoscope 2, it is possible to rotate a distal end of the tube 6 about the second pivot 12.

Here, the operating part main body 18 is advanced or retracted with respect to the base member 23 and the amount the capturing part 7 protrudes from the distal end of the tube 6 is adjusted. Then, the second lock mechanism 22 is operated to fix a relative position between the tube 6 and the sheath 17. When the tube 6 and the sheath 17 whose relative position is fixed in this manner are pulled to the proximal end side, the moving member 5 rotates about the second pivot 12, as shown in FIG. 3, and the tube 6 approaches a side surface of the mounting part 8 and in the axis direction of the endoscope 2. In addition, depending on the amount of protrusion from the tube 6 of the sheath 17, the capturing part 7 has a position in the vicinity of the cap 9 or in the vicinity of the mounting part 8 adjacent to the cap 9. Therefore, the capturing part 7 is arranged in a side surface of the distal end member 3 while the first pivot 21 is positioned at a hand side relative to the second pivot 12, and the tube 6 and the sheath 17 are arranged substantially in the axis direction of the endoscope 2. In this case, since the connecting member 4 is shaped to follow an outer shape of the distal end member 3, for example, compared to a size of the capturing part 7, the amount the connecting member 4 protrudes from the outer shape of the distal end member 3 is small. Therefore, the size of an outer shape of the entire treatment tool 1 for an endoscope does not increase when the connecting member 4 protrudes.

When the distal end member 3 is mounted, although not shown, the treatment tool 1 for an endoscope and the endoscope 2 are inserted from a patient's mouth to near a lesion part serving as a target portion, and a needle (not shown) passes through the working channel 25 of the endoscope 2. Next, the needle is introduced into submucosae from a near side of the lesion part, a normal saline is injected to the submucosae, and thus the lesion part is raised. Subsequently, for example, the high frequency knife is introduced through the endoscope and a hole is made in a part of mucosae in the vicinity of the lesion part to perform initial incision. Further, in this state, the high frequency knife is moved while a high frequency current is supplied, and the hole of initial incision is set to be wider to a predetermined size. In this manner, the state shown in FIG. 6 is obtained. That is, a cut end CU is positioned in front (the left side of FIG. 6) of the endoscope 2 on which the distal end member 3 is mounted, and a mucosa M including a lesion part X is positioned on a submucosa S further in front of the cut end CU.

Next, from between the cut ends CU in this state, a high frequency knife different from that described above is brought in contact with the submucosa S of the lesion part X to cut and dissect it. For this purpose, first, the base member 23 of the second lock mechanism 22 is used to advance the tube 6 and the sheath 17. Accordingly, as shown in FIG. 7, the connecting member 4 rotates forward about the second pivot 12. Therefore, the first pivot 21 moves along an arc $C_1$ using the second pivot 12 as a center. As a result, the moving member 5 coupled to the first pivot 21 is moved forward along a trajectory of the first pivot 21. In other words, a linear movement of the advancing of the tube 6 and the sheath 17 is converted into a rotating movement along the arc $C_1$ by the connecting member 4. In this case, the sheath 17, the support member 14, and the capturing part 7 of parts protruding from the moving member 5 also perform a rotating movement together with the moving member 5.

In this manner, a distal end part of the capturing part 7 advances from an accommodating position (refer to FIG. 6), which is a position in an initial state, while being separated from the distal end member 3. Further, when the first pivot 21 moves to a distal end side relative to the second pivot 12, the distal end part moves forward and toward a central part of the distal end member 3 along the arc $C_1$, and approaches the mucosa M in front of the endoscope 2. In this case, since the capturing part 7 enters a field of view of the observation device 26 in the endoscope 2, it is possible to observe a movement state of the capturing part 7 and the like through the observation device 26. When the connecting member 4 further rotates, the capturing part 7 approaches the mucosa M. Therefore, when a position of the endoscope 2 on the mucosa M is appropriately set, the capturing part 7 can be positioned at a position of the cut end CU. When it is checked that the pair of forceps members 15A and 15B of the capturing part 7 arrive at the cut end CU through an image of the observation device 26, the tube 6 and the sheath 17 stop advancing.

Next, the slider 19 of the operating part 16 is advanced or retracted to open or close the pair of forceps members 15A and 15B. Accordingly, as shown in FIG. 7, tissues of the mucosa M including the lesion part X within the cut end CU are captured and grasped by the grasping part 15a of the forceps members 15A and 15B. In this case, since the forceps members 15A and 15B are within the field of view of the observation device 26, it is possible to check whether the grasping state is appropriate through the observation device 26. When there is a problem in the grasping state, a position of the capturing part 7 is finely adjusted, and capturing and grasping are performed again. In this manner, when grasping of the tissues is completed, while the first lock mechanism 20 abuts the slider 19, an outer circumferential part of the first lock mechanism 20 is rotated, and a position of the slider 19 with respect to the operating part main body 18 is fixed. Accordingly, since the slider 19 is prevented from returning, even when a hand is separated from the slider 19, the pair of forceps members 15A and 15B are not opened, but maintain a closed state. As a result, it is possible to prevent the grasped tissues from being separated.

Next, as shown in FIG. 8, without changing a position of the endoscope 2, the tube 6 and the sheath 17 are retracted to the proximal end side. Accordingly, the connecting member 4 rotates about the second pivot 12, and the distal end part of the capturing part 7 is returned in a direction away from the lesion part X. Therefore, tissues of the periphery of the cut end CU are pulled upward in the drawing, and the mucosa M is lifted up. Accordingly, since the capturing part 7 is moved to the outside of the field of view of the observation device 26, a field of view in front of the observation device 26 is ensured. Therefore, it is possible to observe the pulled submucosa S entirely. In this state, a high frequency knife 27 is drawn from the working channel 25 to the vicinity of the front submucosa S. As necessary, a bending manipulation of the endoscope 2 is performed, the high frequency knife 27 is moved, and the submucosa S is cut and dissected.

When cutting and dissecting proceed, since a length of the lifted mucosa M increases, the mucosa M becomes loose and covers the high frequency knife 27. In this case, when engagement of the second lock mechanism 22 is released and the sheath 17 is advanced to the tube 6, as shown in FIG. 9, it is possible to turn the mucosa M back in a facing direction. When the above-described operations are repeated and tissues in the vicinity of the lesion part X are completely resected, the lesion part X is grasped and collected by a forceps member (not shown) inserted from the working channel 25 or the like, and treatment ends.

According to the present embodiment, in addition to moving the capturing part 7 by rotating the connecting member 4 about the second pivot 12, the capturing part 7 can be advanced and retracted independently from a rotating operation of the connecting member 4 in front of the moving member 5 by the sheath 17 held by the tube 6 in an advanceable and retractable manner. Therefore, the capturing part 7 can be moved from the accommodating position at a side of the distal end member 3 to a position around the front of the distal end member 3 and the endoscope 2, past respective central axes of the distal end member 3 and the endoscope 2, and at which tissues are grasped. In addition, after the tissues are grasped, only the capturing part 7 is advanced and the mucosa M is turned back. Therefore, it is possible to ensure a sufficient field of view when the submucosa S is cut and apply appropriate tension to the submucosa S.

Figure 10:
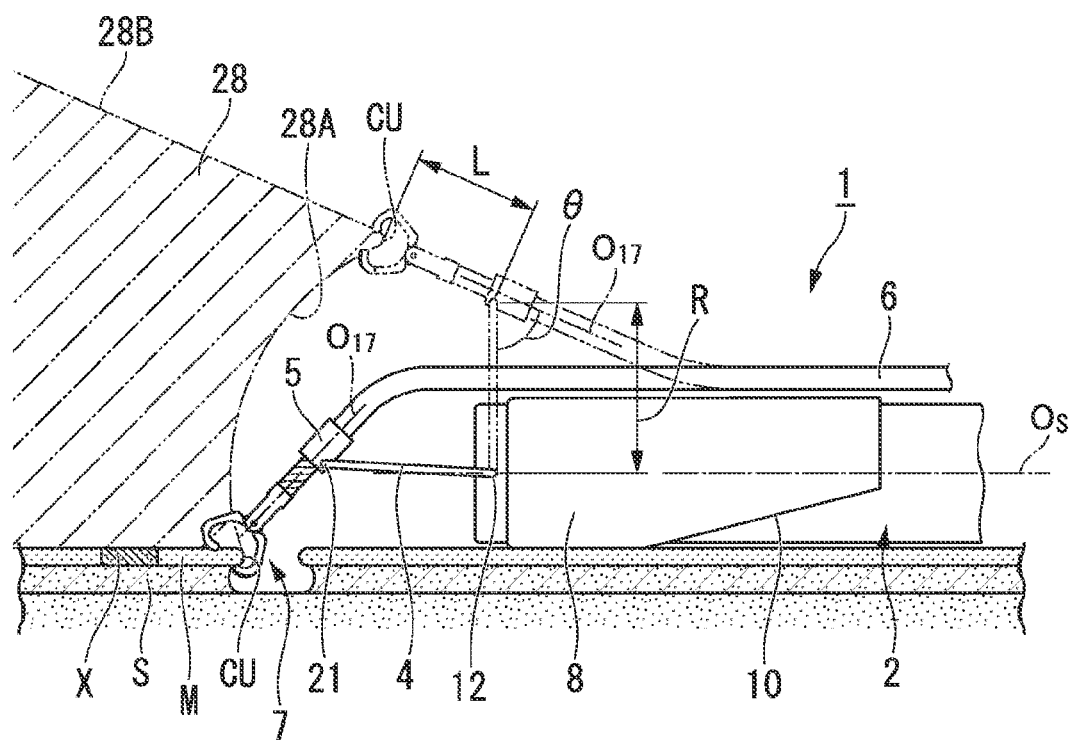
FIG. 10 is a diagram schematically showing an operation range of the treatment part of the treatment tool for an endoscope according to the first embodiment of the present invention.
Figure 11:
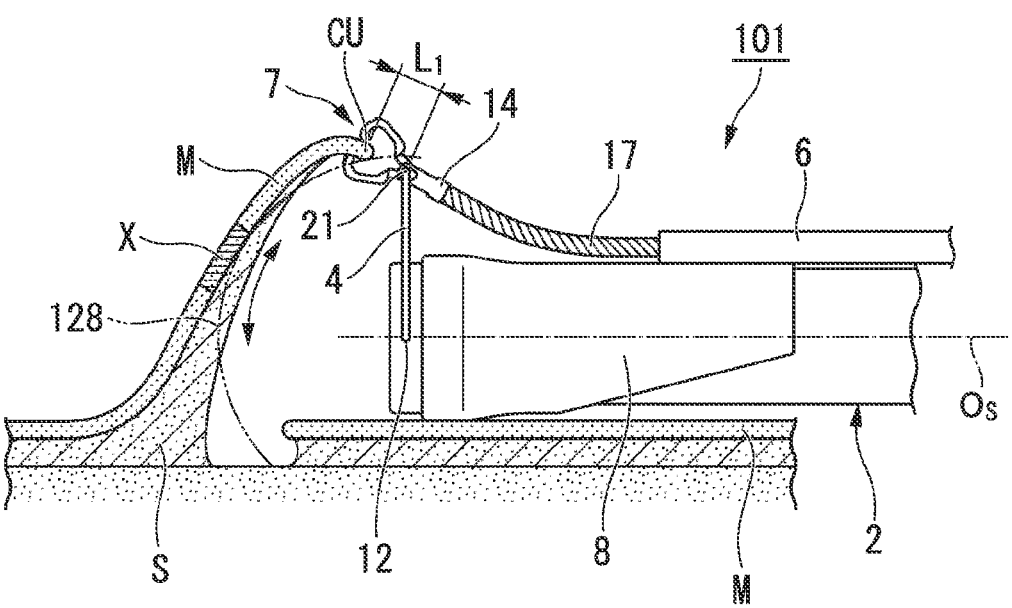
FIG. 11 is a diagram schematically showing an operation range of a treatment part of a treatment tool for an endoscope of Comparative Example 1.
Figure 12:
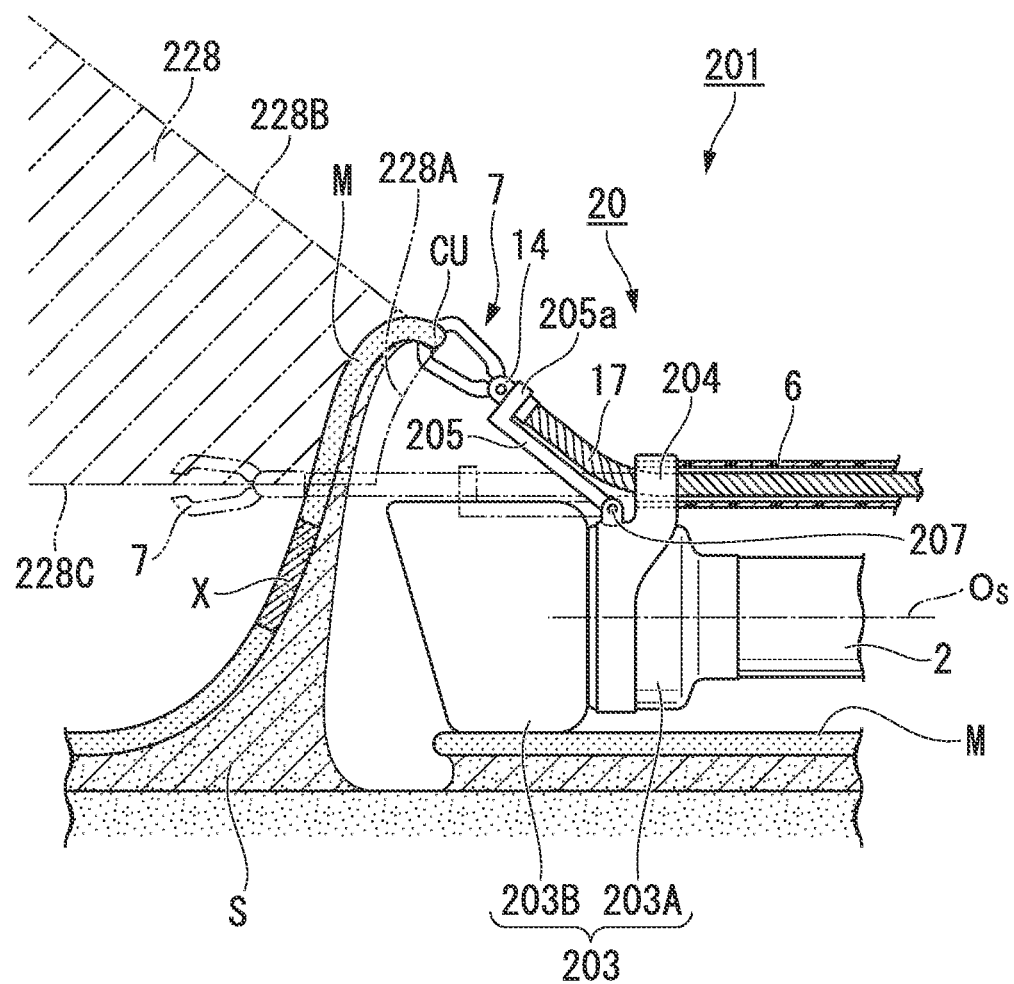
FIG. 12 is a diagram schematically showing an operation range of a treatment part of a treatment tool for an endoscope of Comparative Example 2.

Here, a moving region of the capturing part 7 in the treatment tool 1 for an endoscope will be comparatively described with Comparative Examples. FIG. 10 is a diagram schematically showing an operation range of the treatment part of the treatment tool for an endoscope according to the first embodiment of the present invention. FIG. 11 is a diagram schematically showing an operation range of a treatment part of a treatment tool for an endoscope of Comparative Example 1. FIG. 12 is a diagram schematically showing an operation range of a treatment part of a treatment tool for an endoscope of Comparative Example 2.

A movable region 28 shown in FIG. 10 shows a movable range of a grasping position by the capturing part 7 of the treatment tool 1 for an endoscope. However, to compare a movable range in front of the endoscope 2, a movable range when the connecting member 4 is tilted to the proximal end side is not shown. Here, a protrusion distance from a distal end of the moving member 5 to the cut end CU grasped by the capturing part 7 is set as L. A rotating radius (an inter-axial distance between the second pivot 12 and the first pivot 21) using the second pivot 12 of the connecting member 4 as a center is set as R. An angle formed by the connecting member 4 and a central axis $O_{17}$ of the sheath 17 is set as θ. Since the moving member 5 and the connecting member 4 are rotatably coupled by the first pivot 21, the angle θ does not necessarily have a constant value, but the angle θ is changed only within an acute angle range due to a resistance force against a curvature of the tube 6 and the sheath 17 when rotating is performed in front of the endoscope 2. Accordingly, for simplicity, FIG. 10 shows a case in which the angle θ is constant.

An arc 28A is a movement trajectory of the cut end CU when the protrusion distance L has a minimum value. A straight line 28B is a movement trajectory of the cut end CU when the protrusion distance L is changed while the connecting member 4 is fixed to a position (refer to a two-dot chain line shown in the drawing) perpendicular to the central axis $O_S$ of the endoscope 2. It is apparent that, when the protrusion distance L increases while the connecting member 4 is tilted further forward, the cut end CU moves any oblique region surrounded by the mucosa M, the arc 28A, and the straight line 28B. Therefore, the movable region 28 in the treatment tool 1 for an endoscope includes a front region including the field of view of the endoscope 2 on the mucosa M and an oblique front area of the endoscope 2 including a region outside the field of view of the endoscope 2 on the mucosa M. Therefore, in front of the endoscope 2, the capturing part 7 can be moved within the field of view of the endoscope 2, and retracted to the outside of the field of view of the endoscope 2. For example, even when the endoscope 2 is not arranged to be sufficiently close to the lesion part X, it is possible to grasp the cut end CU further forward without changing a position of the endoscope 2 by increasing the amount the sheath 17 protrudes.

The treatment tool 101 for an endoscope of Comparative Example 1 shown in FIG. 11 has a configuration in which the moving member 5 of the treatment tool 1 for an endoscope according to the present embodiment is removed, the connecting member 4 and the support member 14 are rotatably coupled by the first pivot 21, and the tube 6 is fixed to the side surface of the mounting part 8. The treatment tool 101 for an endoscope corresponds to a device of the related art disclosed in, for example, Japanese Patent No. 4980777.

According to the treatment tool 101 for an endoscope, the cut end CU is grasped at a position that is separated only a constant distance $L_1$ (where $L_1<L$) from the first pivot 21 by the capturing part 7, and can move in only a linear region of an arc 128 having the second pivot 12 as a center. Accordingly, when the cut end CU is not positioned along the arc 128, since the endoscope 2 itself is moved and the position needs to be aligned, workability significantly decreases compared to the treatment tool 1 for an endoscope. In addition, when incision proceeds and the mucosa M becomes loose, since the cut end CU can be pulled up only along the arc 128, if it is pulled upward along the central axis $O_S$ of the endoscope 2, the mucosa M approaches the endoscope 2. Therefore, a space in front of the endoscope 2 for performing treatment decreases in size and workability decreases.

In a treatment tool 201 for an endoscope of Comparative Example 2 shown in FIG. 12, the connecting member 4 and the moving member 5 of the treatment tool 1 for an endoscope according to the present embodiment are removed, and a distal end member 203 is included in place of the distal end member 3. The treatment tool 201 for an endoscope corresponds to a device of the related art disclosed in, for example, Japanese Unexamined Patent Application, First Publication No. 2012-24597.

The distal end member 203 includes a soft hood 203A, a rigid cap part 203B, and a support part 204. The hood 203A is mounted at a distal end of the endoscope 2. The cap part 203B is formed in a tubular shape that extends forward from the hood 203A. A distal end of the cap part 203B is tilted in a direction intersecting an extending direction. The support part 204 fixes the distal end of the tube 6 to a side part of the hood 203A. In the vicinity of the support part 204 at the hood 203A side, in order to rotatably support a link member 205, a rotation shaft 207 extending in a direction perpendicular to a position that is twisted with respect to the central axis $O_S$ of the endoscope 2 is provided.

The link member 205 has one end that is rotatably coupled to the rotation shaft 207 and the other end provided with an annular part 205a into which the support member 14 and the sheath 17 can be inserted. In such a configuration, in the treatment tool 201 for an endoscope, the sheath 17 exposed from the tube 6 is inserted into the annular part 205a of the link member 205. The capturing part 7 coupled to the distal end of the sheath 17 through the support member 14 is supported so as to advance and retract in an extending direction of the link member 205. The link member 205 can change a rotating position by the operating part 16 to which an operating mechanism (not shown) is coupled.

According to the treatment tool 201 for an endoscope of Comparative Example 2 in this manner, when the sheath 17 is advanced or retracted, a position of the capturing part 7 can be moved to a front position relative to the annular part 205a, and when the link member 205 rotates about the rotation shaft 207, it is possible to rotate the capturing part 7 and the sheath 17 about the rotation shaft 207. Therefore, the capturing part 7 is moved in a range of a movable range 228 shown in FIG. 12, and the cut end CU can be grasped and moved. The movable range 228 is a region surrounded by an arc 228A, a straight line 228C, and a straight line 228B. When a protrusion distance from the annular part 205a has a minimum value, the arc 228A is a trajectory of a distal end of the capturing part 7 when the link member 205 is rotated. The straight line 228C is a straight line along a generating line of a side surface of the cap part 203B. The straight line 228B is a straight line that extends in a direction in which the link member 205 extends when the link member 205 is rotated toward the side to a maximal extent.

According to the treatment tool 201 for an endoscope, since a front region facing an opening of the cap part 203B along the central axis $O_S$ of the endoscope 2 is not included in the movable range 228, it is not possible to move the capturing part 7 to the region. Therefore, since the observation device 26 of the endoscope 2 is unable to observe a state in which the capturing part 7 grasps the cut end CU, workability significantly decreases compared to the treatment tool 1 for an endoscope.

In this manner, in the treatment tool 1 for an endoscope according to the present embodiment, the capturing part 7 is fixed to the distal end of the sheath 17 that is inserted into the tube 6 and can advance and retract, and the connecting member 4 that is pivotally coupled by the second pivot 12 with respect to the distal end member 3 and pivotally coupled by the first pivot 21 with respect to the tube 6 is included. Therefore, the second pivot 12 can rotate the connecting member 4 such that the first pivot 21 is moved from a position at the proximal end side relative to the second pivot 12 and at a side of the distal end member 3 to a position at a distal end side relative to the second pivot 12. Accordingly, even when a position of the endoscope 2 is fixed, the moving region of the capturing part 7 is a region of a wide range including the field of view of the endoscope 2. Therefore, it is possible to increase the workability.

In other words, the treatment tool 1 for an endoscope is configured such that, in addition to moving the capturing part 7 by the connecting member 4, the capturing part 7 is moved independently from the connecting member 4. Therefore, it is possible to move the capturing part 7 from the accommodating position along the distal end member 3 to a position beyond central axes of the distal end member 3 and the endoscope 2 and at which biological tissues are grasped. Accordingly, for example, after biological tissues are grasped, only the capturing part 7 is advanced and the mucosa M is turned back. Therefore, it is possible to ensure a sufficient field of view when the submucosa S is cut and apply appropriate tension to the submucosa S.

In addition, when the cap 9 is mounted on the endoscope, the treatment tool 1 for an endoscope can be integrally handled with the endoscope 2. When the cap 9 is removed, the endoscope 2 can be used alone.

Second Embodiment

Figure 13:
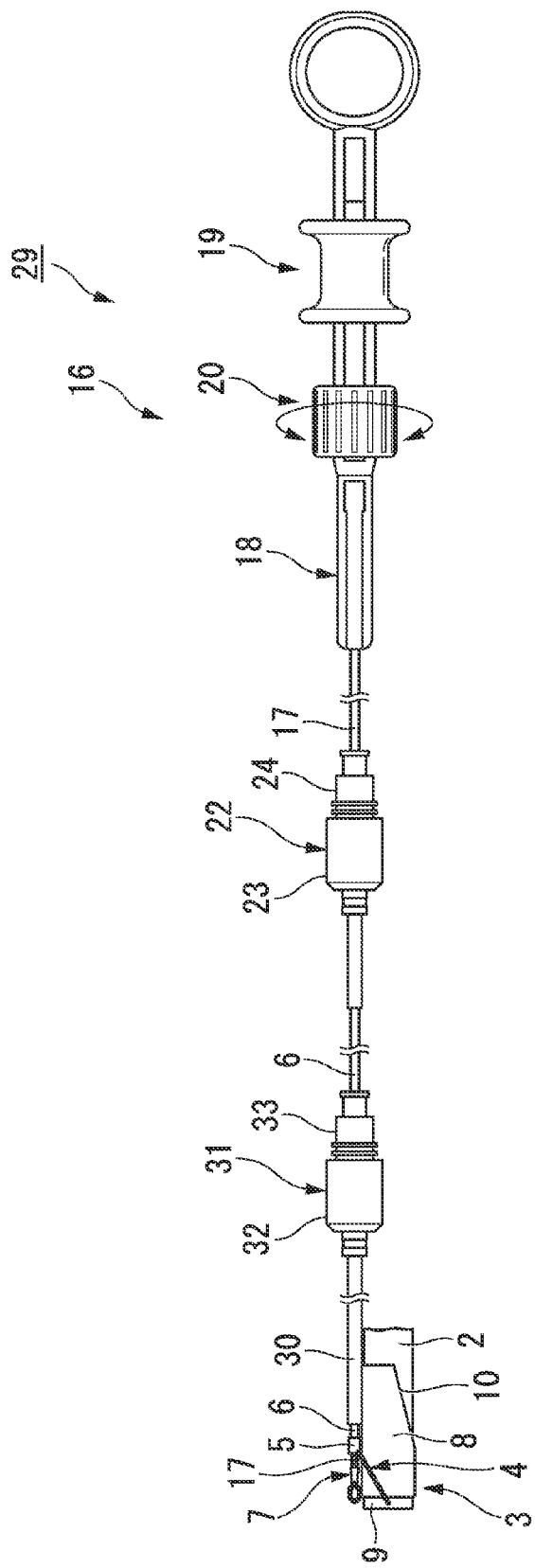
FIG. 13 is a front view schematically showing a treatment tool for an endoscope according to a second embodiment of the present invention.
Figure 14:
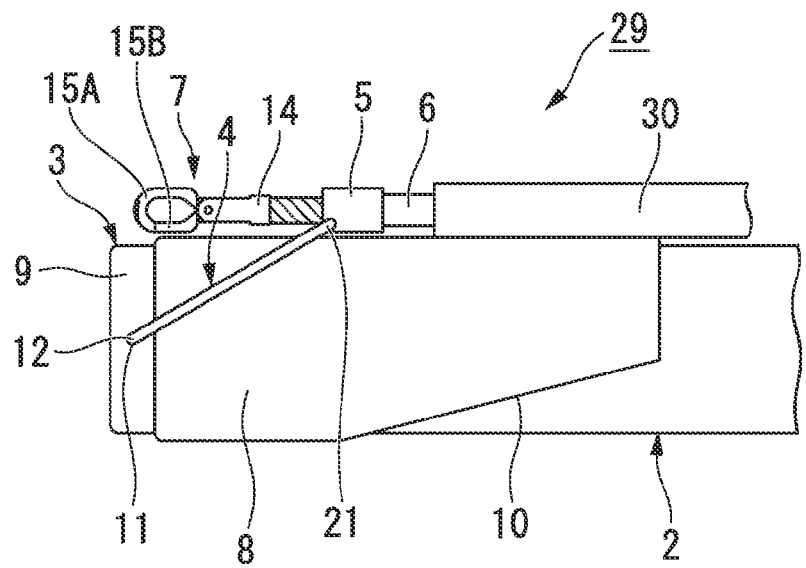
FIG. 14 is a front view schematically showing a state in which a distal end member and a treatment part of a treatment tool for an endoscope according to the second embodiment of the present invention are mounted on an endoscope.
Figure 15:
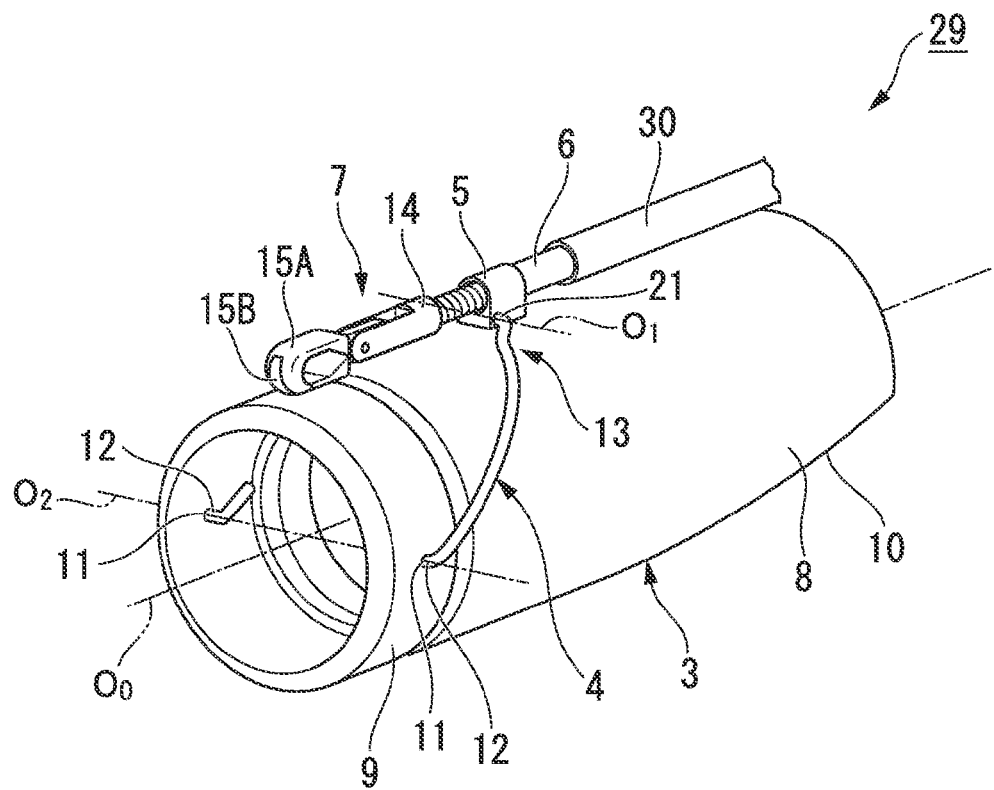
FIG. 15 is a perspective view schematically showing a main part of the treatment tool for an endoscope according to the second embodiment of the present invention.

A treatment tool for an endoscope according to the second embodiment of the present invention will be described. FIG. 13 is a front view schematically showing a treatment tool for an endoscope according to the second embodiment of the present invention. FIG. 14 is a front view schematically showing a state in which a distal end member and a treatment part of a treatment tool for an endoscope according to the second embodiment of the present invention are mounted on an endoscope. FIG. 15 is a perspective view schematically showing a main part of the treatment tool for an endoscope according to the second embodiment of the present invention.

As shown in FIGS. 13 to 15, a treatment tool 29 for an endoscope according to the present embodiment further includes an external tube 30 (coating part) and a third lock mechanism 31 in addition to the configuration of the treatment tool 1 for an endoscope according to the first embodiment. Hereinafter, descriptions will be provided focusing on content different from that of the first embodiment.

The external tube 30 is formed of a tubular member having flexibility into which the tube 6 can be inserted. A distal end part of the external tube 30 is adhered and fixed to a side surface of the mounting part 8. An adhesion position of the external tube 30 is a position shifted 90° on a circumference of the distal end member 3 from a position at which each of the pair of holes 11 (refer to FIGS. 14 and 15) supporting the connecting member 4 is formed, at a substantially opposite side of the slit 10. The external tube 30 forms a coating part into which the tube 6 is inserted in an advanceable and retractable manner.

The third lock mechanism 31 is configured to switch disengagement between the external tube 30 and the tube 6. As shown in FIG. 13, the third lock mechanism 31 is provided at a proximal end of the external tube 30. The third lock mechanism 31 includes a base member 32 fixed to the external tube 30 and an engaging member 33 that can be disengaged from the base member 32.

The engaging member 33 is provided so as to approach or separate from the tube 6 at an outer circumference side of the tube 6. When the engaging member 33 is engaged with the base member 32, the engaging member 33 comes in close contact with an outer circumference of the tube 6, and a position of the tube 6 with respect to the engaging member 33 is fixed. In this case, the tube 6 has a relatively fixed position with respect to the external tube 30 fixed to the base member 32 engaged with the engaging member 33, and relative rotation and advancing and retraction with respect to the external tube 30 are impossible. That is, the third lock mechanism 31 is locked and a position of the tube 6 is fixed. When engagement of the base member 32 with the engaging member 33 is released and the engaging member 33 is detached from the base member 32, since the engaging member 33 is separated from the tube 6, it is possible to advance and retract the tube 6 with respect to the external tube 30. That is, the third lock mechanism 31 is unlocked and the tube 6 is movable.

Next, the treatment tool 29 for an endoscope according to the present embodiment will be described focusing on operations different from the treatment tool 1 for an endoscope according to the above-described first embodiment. First, in a manner similar to the first embodiment, the mounting part 8 of the treatment tool 29 for an endoscope is mounted on a distal end part of the endoscope 2 by adjusting a position thereof. The amount the capturing part 7 protrudes from the distal end of the tube 6 is adjusted, and the tube 6 and the sheath 17 are fixed by the second lock mechanism 22. Next, while the third lock mechanism 31 is unlocked, the tube 6 and the sheath 17 are pulled to the proximal end side. Then, the third lock mechanism 31 is operated to fix a relative position between the external tube 30 and the tube 6.

Next, similarly to first embodiment, the treatment tool 29 for an endoscope is moved to near the lesion part X, and the cut end CU is formed. When the submucosa S of the lesion part X is cut and dissected, the third lock mechanism 31 is unlocked, and the tube 6 and the sheath 17 are advanced with respect to the external tube 30. When the tube 6 is fixed at a position at which advancement stops, the third lock mechanism 31 can be operated to fix the tube 6. Operations other than the above operations are the same as those of the first embodiment.

The treatment tool 29 for an endoscope according to the present embodiment includes the external tube 30 whose distal end is fixed to the mounting part 8 and whose proximal end is provided with the third lock mechanism 31 in an outer circumferential part of the tube 6. Therefore, at positions in which the tube 6 and the sheath 17 are moved, the tube 6 and the sheath 17 are fixed by the third lock mechanism 31, and thus a position of the capturing part 7 can be maintained. Accordingly, there is no need to hold the tube 6 and the sheath 17 by hand, and it is possible to perform the procedure more easily. In addition, since the tube 6 and the sheath 17 move inside the external tube 30, these movements become smooth without deflection.

Third Embodiment

Figure 16:
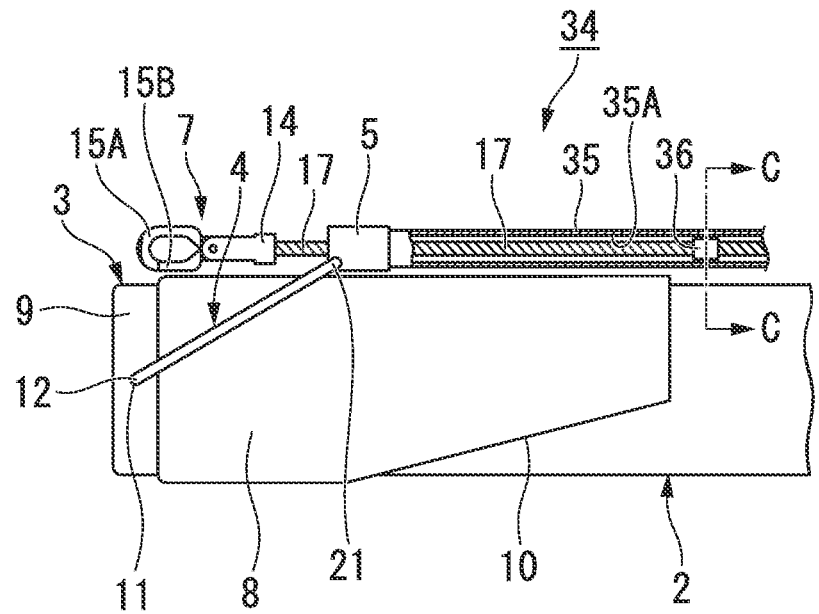
FIG. 16 is a front view schematically showing a state in which a distal end member and a treatment part of a treatment tool for an endoscope according to a third embodiment of the present invention are mounted on an endoscope.
Figure 17:
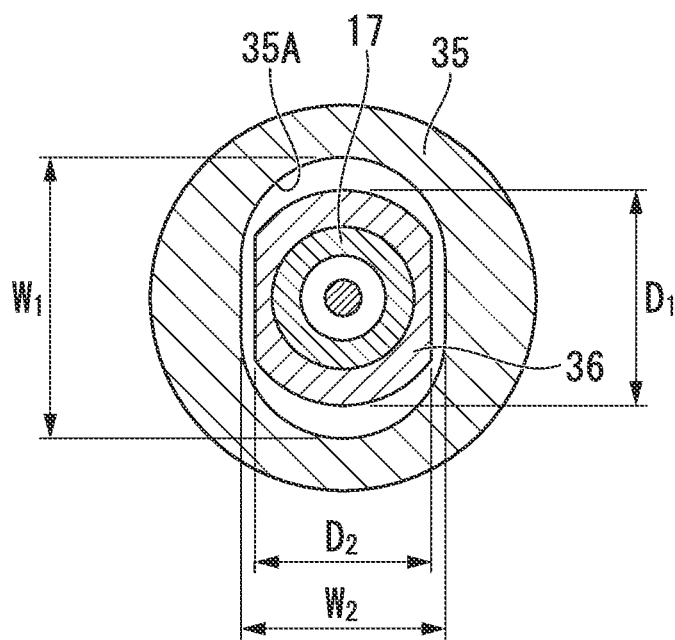
FIG. 17 is a cross sectional view along C-C in FIG. 16.

A treatment tool for an endoscope according to the third embodiment of the present invention will be described. FIG. 16 is a front view schematically showing a state in which a distal end member and a treatment part of a treatment tool for an endoscope according to third embodiment of the present invention are mounted on an endoscope. FIG. 17 is a cross sectional view along C-C in FIG. 16.

As shown in FIGS. 16 and 17, a treatment tool 34 for an endoscope according to the present embodiment includes a tube 35 in place of the tube 6 of the treatment tool 1 for an endoscope according to the first embodiment, and further includes a direction regulating member 36. Hereinafter, descriptions will be provided focusing on content different from that in the first embodiment.

The tube 35 is formed of a tubular member having flexibility into which the sheath 17 can be inserted and has a deformed lumen 35A (lumen) whose cross sectional shape is different from a circular shape. In the present embodiment, as one example, the cross sectional shape of the deformed lumen 35A is an oval shape whose longitudinal width is $W_1$ and whose short width is $W_2$ (where $W_2<W_1$) as shown in FIG. 17.

The direction regulating member 36 is a member that is fixed to an outer circumferential part of the sheath 17 in order to regulate rotation of the sheath 17 inserted into the deformed lumen 35A of the tube 35 inside the deformed lumen 35A. A fixing position of the direction regulating member 36 with respect to the sheath 17 is selected from a range that is not exposed externally from the tube 35. In addition, the number of direction regulating members 36 is not limited to one, and a plurality of direction regulating members 36 may be separated from each other and fixed to the sheath 17.

As long as a cross sectional shape of the direction regulating member 36 has anisotropy through which rotation about a central axis of the deformed lumen 35A is regulated within a constant range and can be advanced and retracted in a central axis direction, it is not particularly limited. In the present embodiment, as one example, as shown in FIG. 17, as the direction regulating member 36, an annular member whose outer circumferential surface has an oval shape with a longitudinal width of $D_1$ (where $D_1<W_1$) and a short width of $D_2$ (where $D_2<W_2$) and whose inner circumferential surface has a circular hole shape that can be fixed to an outer circumference of the sheath 17 is used.

A dimensional difference between the longitudinal width $W_2$ of the deformed lumen 35A and the longitudinal width $D_2$ of the direction regulating member 36 can be appropriately set such that a rotating range of the direction regulating member 36 depending on a gap corresponding to the dimensional difference is within an allowable range. A length and the short width $D_2$ of the direction regulating member 36 can be set as appropriate sizes at which the direction regulating member 36 can smoothly move along a central axis within the deformed lumen 35A even when the tube 35 is curved.

In such a configuration, in the treatment tool 34 for an endoscope, the sheath 17 can be advanced and retracted within the tube 35. In addition, when the sheath 17 is advanced or retracted, even if the sheath 17 is intended to be rotated, the direction regulating member 36 comes in contact with an inner circumferential surface of the deformed lumen 35A of the tube 35, and thus rotation is regulated. Accordingly, positions around a central axis of the tube 35 of the sheath 17 and the capturing part 7 fixed to the distal end of the sheath 17 are regulated as a predetermined range. Therefore, in the treatment tool 34 for an endoscope, a direction of the treatment part fixed to the distal end of the sheath 17 can be maintained as a direction in which treatment is easily performed.

For example, when the treatment part is the capturing part 7, it is possible to set an opening and closing direction of the capturing part 7 to be substantially aligned with a direction in which biological tissues are easily grasped. In the present embodiment, as one example, when a direction of a longitudinal width of the direction regulating member 36 is aligned to fix the direction regulating member 36, the opening and closing direction of the capturing part 7 is aligned with a direction of the longitudinal width of the deformed lumen 35A. Therefore, according to the treatment tool 34 for an endoscope, since the opening and closing direction of the capturing part 7 is relatively fixed with respect to an arrangement direction of the tube 35, for example, an operation in which the sheath 17 is rotated to adjust the opening and closing direction of the capturing part 7 is unnecessary, and an operation of the capturing part 7 grasping biological tissues becomes easier. The other operations of the treatment tool 34 for an endoscope according to the present embodiment are the same as those of the above-described first embodiment.

Fourth Embodiment

Figure 18:
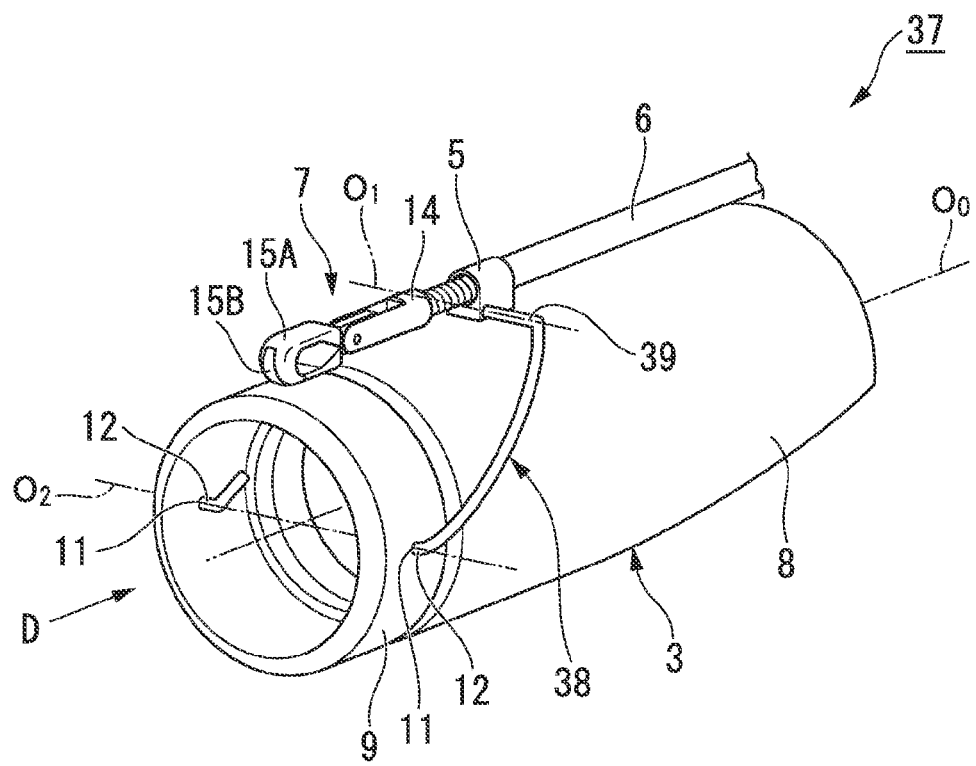
FIG. 18 is a perspective view schematically showing a main part of a treatment tool for an endoscope according to a fourth embodiment of the present invention.
Figure 19:
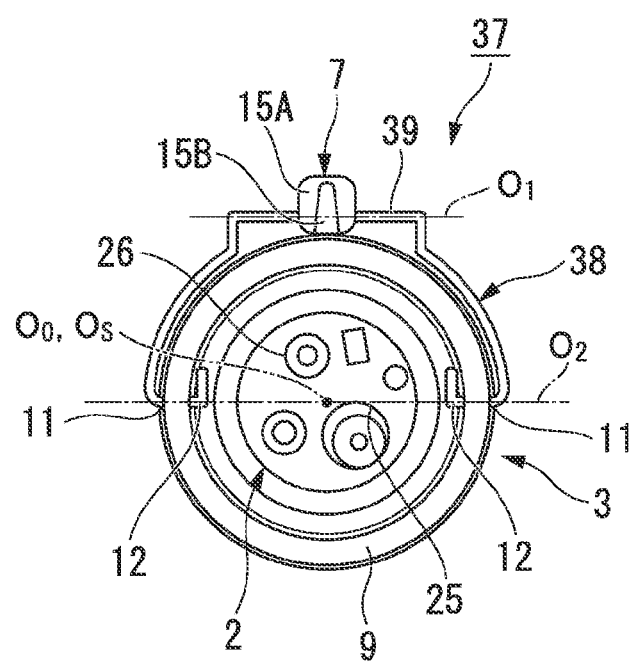
FIG. 19 is a side view corresponding to the arrow D in FIG. 18 when the treatment tool for an endoscope according to the fourth embodiment of the present invention is mounted on an endoscope.
Figure 20:
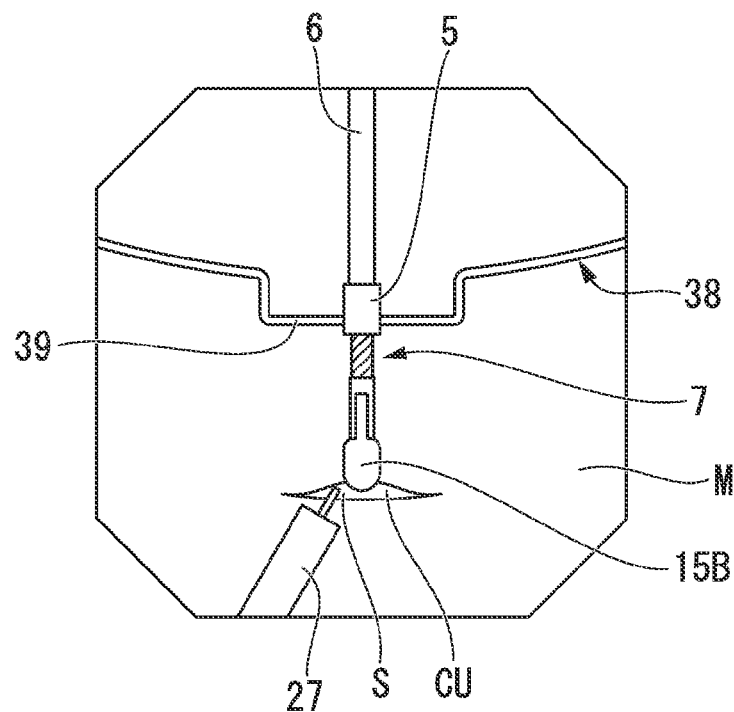
FIG. 20 is a diagram schematically showing one exemplary image observed by an endoscope when a treatment part performs grasping by the treatment tool for an endoscope according to the fourth embodiment of the present invention.
Figure 21:
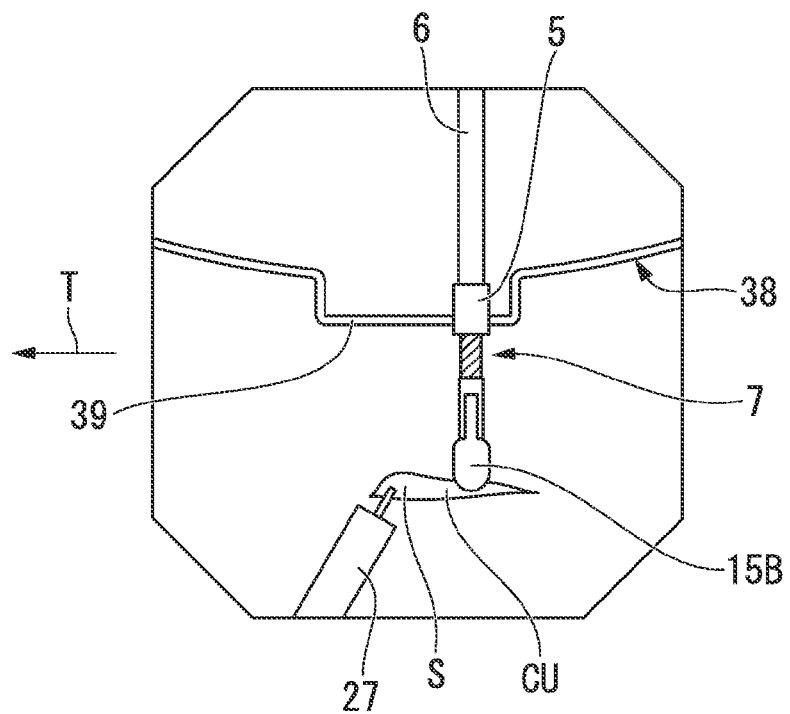
FIG. 21 is a diagram schematically showing one exemplary image of a grasping state of a treatment part that is observed by an endoscope when the endoscope is moved from the state shown in FIG. 20 and incision proceeds.

A treatment tool for an endoscope according to the fourth embodiment of the present invention will be described. FIG. 18 is a perspective view schematically showing a main part of the treatment tool for an endoscope according to the fourth embodiment of the present invention. FIG. 19 is a side view corresponding to the arrow D in FIG. 18 when the treatment tool for an endoscope according to the fourth embodiment of the present invention is mounted on an endoscope. FIG. 20 is a diagram schematically showing one exemplary image observed by an endoscope when a treatment part performs grasping by the treatment tool for an endoscope according to the fourth embodiment of the present invention. FIG. 21 is a diagram schematically showing one exemplary image of a grasping state of a treatment part that is observed by an endoscope when the endoscope is moved from the state shown in FIG. 20 and incision proceeds.

As shown in FIGS. 18 and 19, a treatment tool 37 for an endoscope according to the present embodiment includes a connecting member 38 in place of the connecting member 4 of the treatment tool 1 for an endoscope according to the first embodiment. Hereinafter, descriptions will be provided focusing on content different from that of the first embodiment.

In the connecting member 38, the part 13 of the connecting member 4 according to the first embodiment is bent to a position separated from the moving member 5, and thus a first pivot 39 that is longer than a width of the moving member 5 and longer than the first pivot 21 is formed. Accordingly, as shown in FIG. 18, the moving member 5 can move in a longitudinal direction (direction of the axis $O_1$) of the first pivot 39. Therefore, in the present embodiment, the entire first pivot 39 forms a movement area in which the moving member 5 is movable.

Similarly to the first embodiment, in the treatment tool 37 for an endoscope according to the present embodiment, while the cut end CU is grasped by the capturing part 7, the high frequency knife 27 is drawn from the working channel 25 of the endoscope 2 and the submucosa S can be cut and dissected. In this case, in the treatment tool 37 for an endoscope, it is possible to move the moving member 5 along the first pivot 39. Therefore, when the bending manipulation of the endoscope 2 is performed, the high frequency knife 27 is moved, and incision is performed, an incision direction and a direction of the first pivot 39 are aligned, and incision can be performed while the cut end CU of a certain position is grasped by the capturing part 7.

For example, as a schematically shown image of the observation device 26 in FIG. 20, while the cut end CU is partially formed in the mucosa M in front of the endoscope 2, the cut end CU is grasped by the capturing part 7 and the cut end CU is open. Also, in FIG. 20 (and similarly in FIG. 21), only the field of view of the observation device 26 is shown, and the distal end member 3 and the endoscope 2 are not shown. In this case, an operation in which the high frequency knife 27 is inserted from the endoscope 2 to the submucosa S inside the cut end CU, the mucosa M and the submucosa S are cut, and a length of the cut end CU extends is performed. In order to extend the length of the cut end CU, there is a need to move the endoscope 2 from which the high frequency knife 27 is drawn in the incision direction. In the present embodiment, since the moving member 5 can move along the first pivot 39, as shown in FIG. 21, when the incision direction is aligned with a direction of the first pivot 39, the distal end member 3, the endoscope 2, and the high frequency knife 27 can move in the incision direction (refer to the arrow T in FIG. 21) while positions of the moving member 5, the sheath 17, the tube 6, and the capturing part 7 are fixed. According to this relative movement, the cut end CU is cut in a direction of the arrow T. That is, within the field of view of the observation device 26, the mucosa M, the cut end CU, the capturing part 7, the moving member 5, and the tube 6 relatively move to the opposite side of the shown arrow T, and the cut end CU is cut by the high frequency knife 27 in the direction of the arrow T.

In this manner, while incision is performed, the capturing part 7 does not move with respect to the mucosa M, the submucosa S, and the cut end CU in a range in which the moving member 5 is movable along the first pivot 39. Therefore, while the cut end CU extends, re-grasping the cut end CU by the capturing part 7 is unnecessary and the procedure becomes easier. In addition, while the procedure is performed, tension can be appropriately applied to the submucosa S and thus incision can become easier. The other operations of the treatment tool 37 for an endoscope according to the present embodiment are the same as those of the above-described first embodiment.

First Modified Example and Second Modified Example

Figure 22:
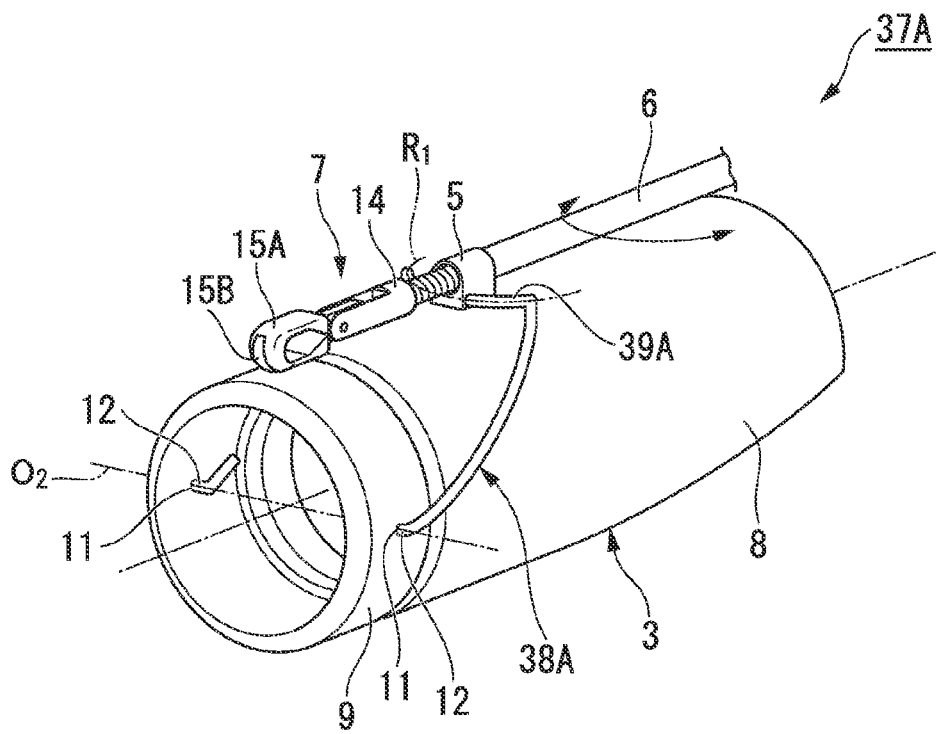
FIG. 22 is a perspective view schematically showing a configuration of a main part of a treatment tool for an endoscope according to a modified example (first modified example) of the fourth embodiment of the present invention.
Figure 23:
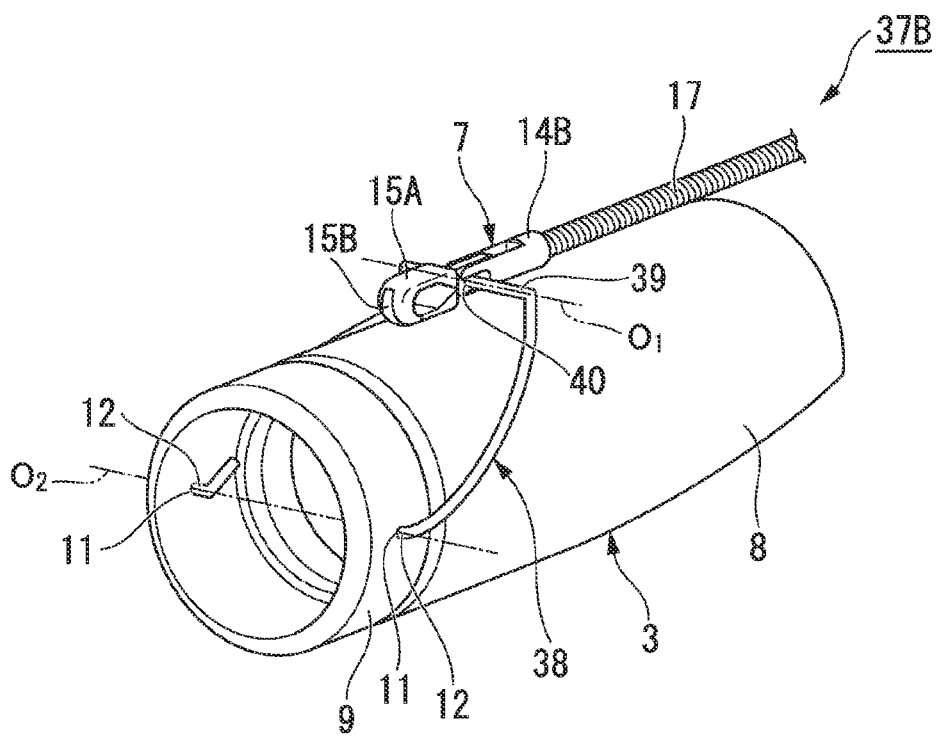
FIG. 23 is a perspective view schematically showing a configuration of a main part of a treatment tool for an endoscope according to a modified example (second modified example) of the fourth embodiment of the present invention.

Next, modified examples (first modified example and second modified example) of the present embodiment will be described. FIG. 22 is a perspective view schematically showing a configuration of a main part of a treatment tool for an endoscope according to a modified example (first modified example) of the fourth embodiment of the present invention. FIG. 23 is a perspective view schematically showing a configuration of a main part of a treatment tool for an endoscope according to a modified example (second modified example) of the fourth embodiment of the present invention.

As shown in FIG. 22, the treatment tool 37A for an endoscope according to the first modified example of the present embodiment includes the connecting member 38A in place of the connecting member 38 according to the fourth embodiment. Hereinafter, descriptions will be provided focusing on content different from that of the fourth embodiment.

The connecting member 38A includes a curved pivot 39A (first pivot) in place of the first pivot 39 of the connecting member 38. The curved pivot 39A has substantially the same length as the first pivot 39 and has an arc shape whose distal end side is convex in the accommodating position as shown in FIG. 22. Therefore, when the endoscope 2 is moved along a curvature of the curved pivot 39A, the moving member 5 can move along the curved pivot 39A. The radius of curvature of a curved line $R_1$, which is a central axis of the curved pivot 39A, can be set as an appropriate radius of curvature depending on an operation of the endoscope 2 while the cut end CU is grasped by the capturing part 7. In the present embodiment, the radius of curvature of the curved line $R_1$ is set to match a rotating radius depending on a bending operation of the endoscope 2. That is, a rotating radius depending on the bending operation of the endoscope 2 when the connecting member 38A rotates about the second pivot 12 and the capturing part 7 is moved to a constant position in front of the endoscope 2 is set as the radius of curvature of the curved pivot 39A.

In the treatment tool 37A for an endoscope according to the present modified example, even when a bending manipulation of the endoscope 2 is performed, the moving member 5 can be relatively smoothly moved along the curved pivot 39A. Therefore, for example, when the bending manipulation of the endoscope 2 is performed and the high frequency knife 27 is operated, the position of the capturing part 7 is likely to be fixed.

As shown in FIG. 23, in the treatment tool 37B for an endoscope according to the second modified example of the present embodiment, the tube 6 and the moving member 5 according to the fourth embodiment are removed, and the support member 14B is included in place of the support member 14. Hereinafter, descriptions will be provided focusing on content different from that of the fourth embodiment.

The support member 14B is configured such that in the support member 14 according to the fourth embodiment, an insertion hole 40 into which the first pivot 39 can be inserted is included and the support member 14B can move in a direction along the axis $O_1$ of the first pivot 39.

According to the treatment tool 37B for an endoscope, the same operations as in the fourth embodiment are provided.

Fifth Embodiment

Figure 24:
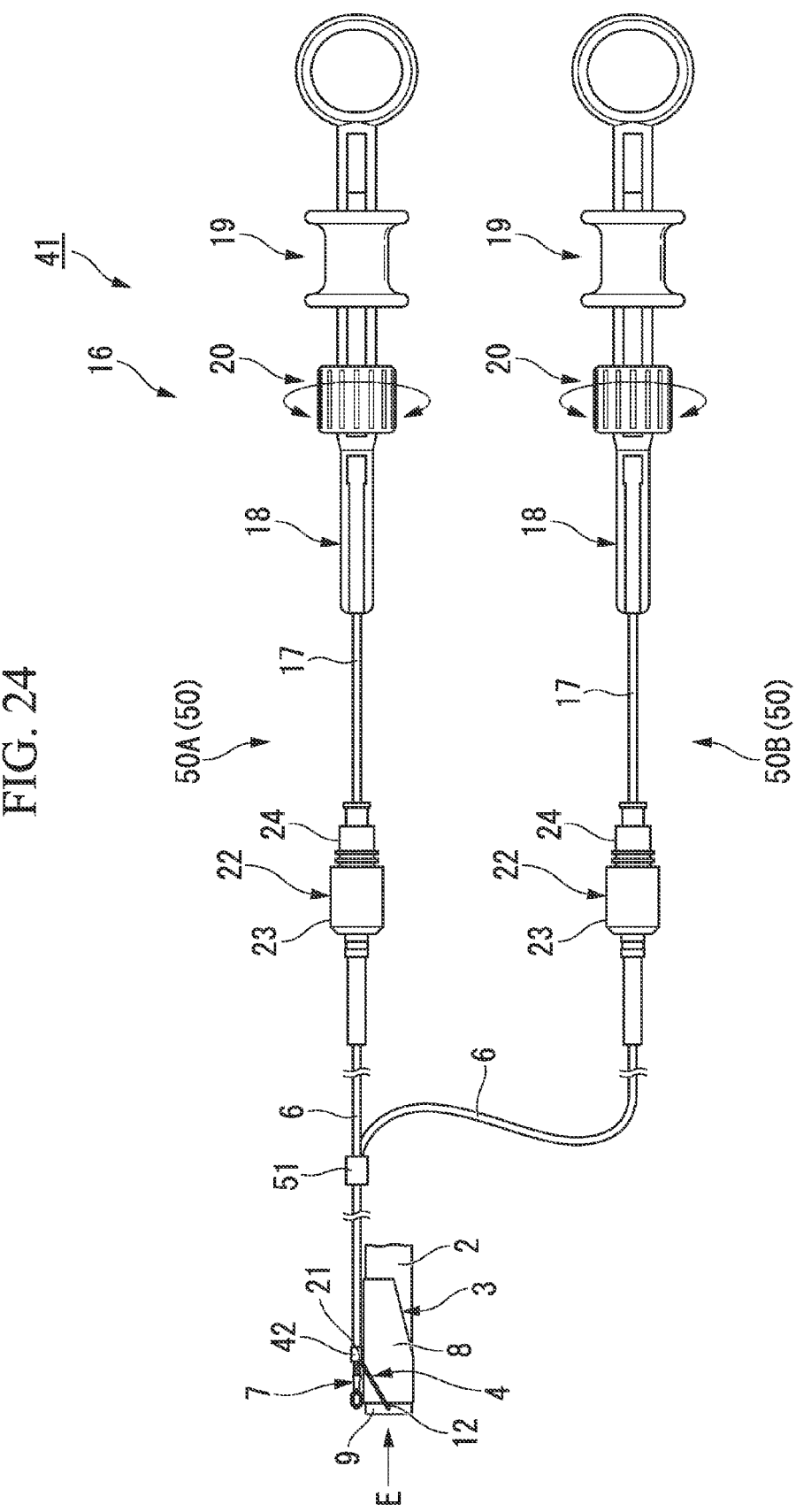
FIG. 24 is a front view schematically showing a state in which a treatment tool for an endoscope according to a fifth embodiment of the present invention is mounted on an endoscope.
Figure 25:
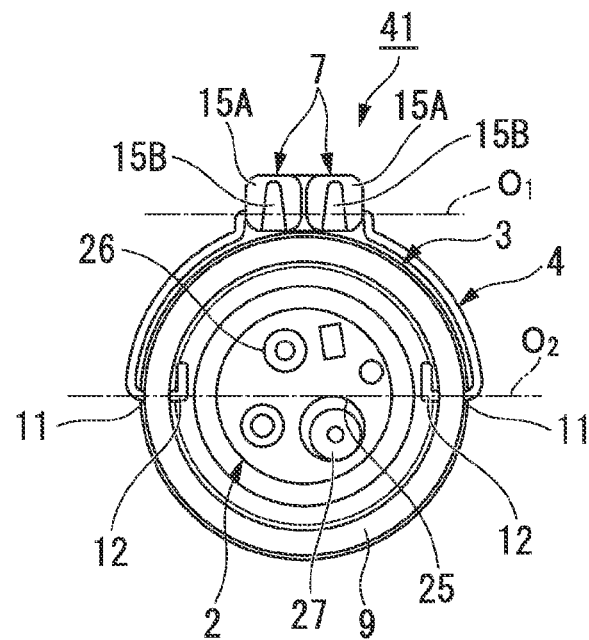
FIG. 25 is a view seen from the arrow E in FIG. 24.
Figure 26:
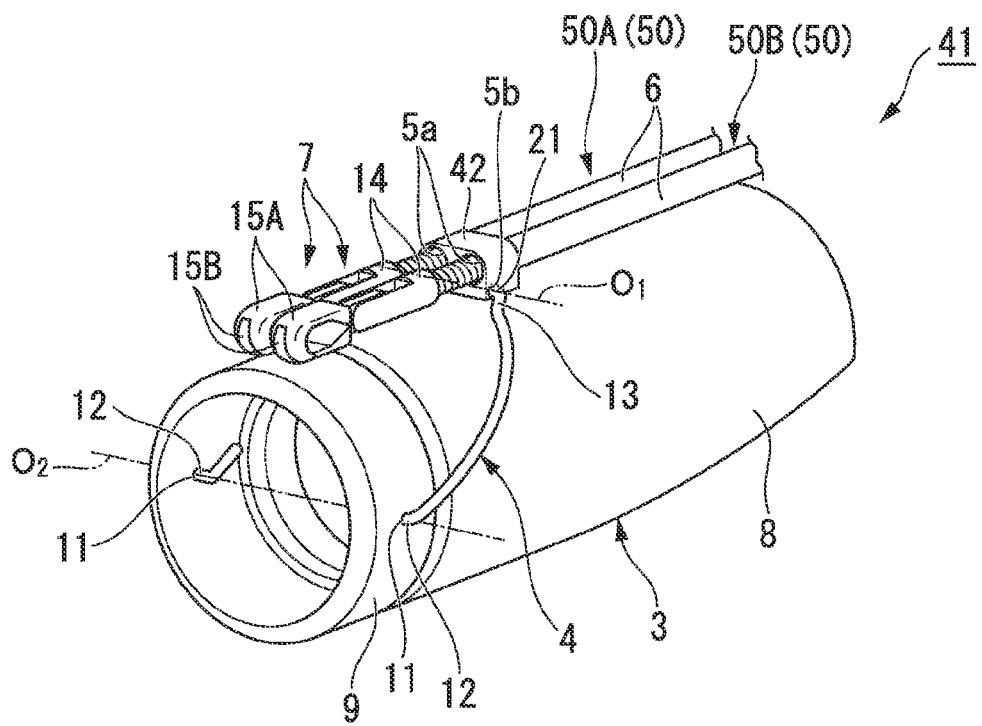
FIG. 26 is a perspective view schematically showing a distal end member and a treatment part of the treatment tool for an endoscope according to the fifth embodiment of the present invention.
Figure 27:
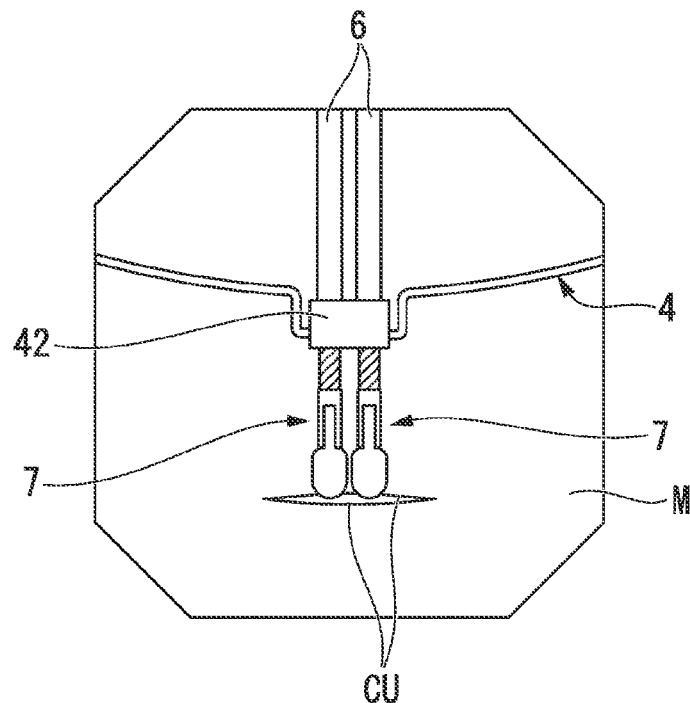
FIG. 27 is a diagram schematically showing one exemplary image observed by an endoscope when the treatment part performs grasping by the treatment tool for an endoscope according to the fifth embodiment of the present invention.
Figure 28:
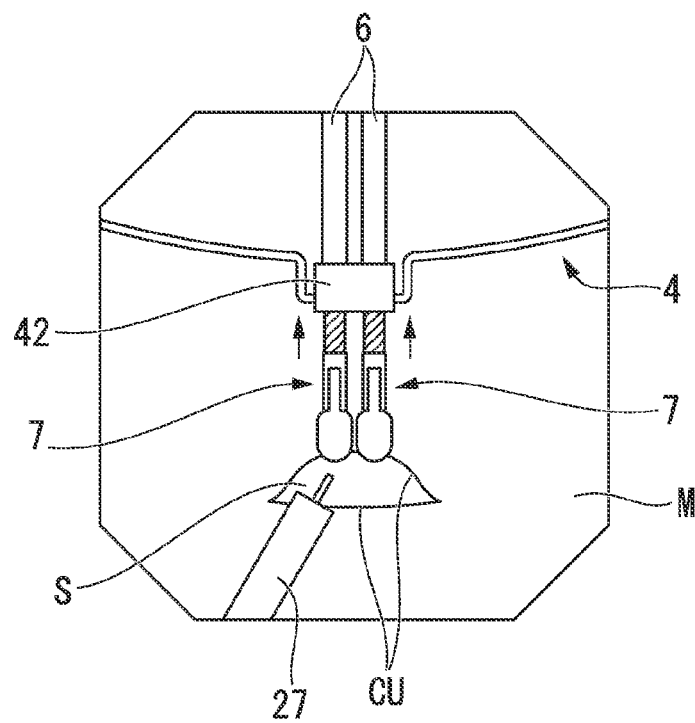
FIG. 28 is a diagram schematically showing one exemplary image observed by an endoscope when a capturing part is moved from the state shown in FIG. 27.

A treatment tool for an endoscope according to the fifth embodiment of the present invention will be described. FIG. 24 is a front view schematically showing a state in which the treatment tool for an endoscope according to the fifth embodiment of the present invention is mounted on an endoscope. FIG. 25 is a view seen from the arrow E in FIG. 24. FIG. 26 is a perspective view schematically showing a distal end member and a treatment part of the treatment tool for an endoscope according to the fifth embodiment of the present invention. FIG. 27 is a diagram schematically showing one exemplary image observed by an endoscope when the treatment part performs grasping by the treatment tool for an endoscope according to the fifth embodiment of the present invention. FIG. 28 is a diagram schematically showing one exemplary image observed by an endoscope when a capturing part is moved from the state shown in FIG. 27.

As shown in FIG. 24, a treatment tool 41 for an endoscope according to the present embodiment includes a moving member 42 in place of the moving member 5 of the treatment tool 1 for an endoscope according to the first embodiment, and further includes a plurality of treatment tool main bodies 50 composed of the capturing part 7, the support member 14, the sheath 17, the tube 6, the second lock mechanism 22, and the operating part 16. The appropriate number of treatment tool main bodies 50 is two or more. In the present embodiment, as one example, the number of treatment tool main bodies 50 is two, the treatment tool main bodies 50A and 50B. Hereinafter, descriptions will be provided focusing on content different from that of the first embodiment.

As shown in FIGS. 25 and 26, the moving member 42 is a member that fixes distal ends of the tubes 6 while the tubes 6 are arranged in parallel in the treatment tool main bodies 50A and 50B, includes the two opening parts 5a and the through-hole 5b (refer to FIG. 26), similarly to the moving member 5 according to the first embodiment, and is rotatably coupled to the connecting member 4. Therefore, the moving member 42 serves as a binding member fixing the distal ends of the two tubes 6. Accordingly, the tubes 6 are arranged substantially in parallel with sides of the mounting part 8 and the endoscope 2 and extend to the proximal end side in the accommodating position. The tubes 6 can be bound by an appropriate binding member at a proximal end side as necessary. In the present embodiment, as one example, as shown in FIG. 24, a binding member 51 is provided at the proximal end side, and an interval of each of the tubes 6 can be freely changed at the proximal end side relative to the binding member 51.

According to the treatment tool 41 for an endoscope, when the connecting member 4 rotates about the second pivot 12, similar to the first embodiment, the two tubes 6 move to the side or front of the endoscope 2 at the same time, and the two capturing parts 7 are accordingly moved. Therefore, for example, as in the image of the observation device 26 schematically shown in FIG. 27, the two capturing parts 7 can grasp the partial cut end CU formed in the mucosa M in front of the endoscope 2 at the same time. In addition, as shown in FIG. 28, the cut end CU grasped by the two capturing parts 7 is simultaneously moved upward in the drawing, the cut end CU is lifted up, and thus the submucosa S can be exposed more widely. In this case, the two capturing parts 7 simultaneously lift the cut end CU up, the cut end CU of a range that is equal to or greater than the same width as an arrangement interval of the two capturing parts 7 is lifted, and thus the cut end CU is largely open. Therefore, for example, treatment by the high frequency knife 27 becomes easier.

Figure 29:
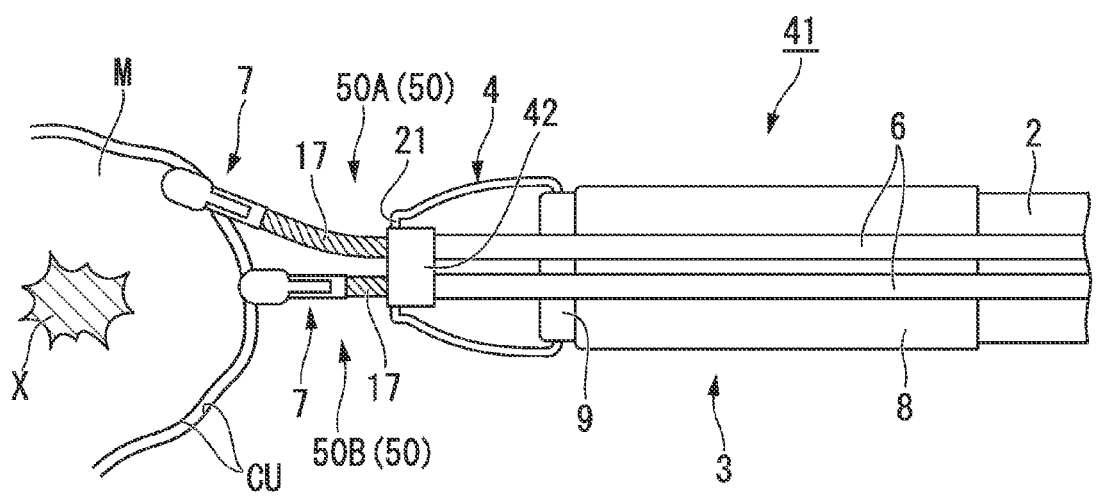
FIG. 29 is an explanatory diagram showing an operation of the treatment tool for an endoscope according to the fifth embodiment of the present invention.

Further, in the treatment tool 41 for an endoscope, since the two capturing parts 7 are coupled to the operating part 16 and the second lock mechanism 22 that can be independently operated through each independent sheath 17, advancing and retraction can be independently performed with respect to each of the tubes 6. In addition, since protrusion lengths of the two capturing parts 7 can be independently changed, as shown in FIG. 29, when a distance between the two capturing parts 7 is appropriately changed and a grasping position or a grasping interval in the cut end CU is appropriately changed, the cut end CU can be grasped. In the example shown in FIG. 29, when a protrusion length of the sheath 17 of the treatment tool main body 50A is set to be greater than a protrusion length of the sheath 17 of the treatment tool main body 50B, a different position in a circumferential direction of the cut end CU formed in a curved shape can be grasped by each of the capturing parts 7.

In the treatment tool 41 for an endoscope according to the present embodiment, since tissues can be more firmly grasped by the two capturing parts 7, when the submucosa S is cut and dissected, the cut end CU is sufficiently enlarged, a sufficient opening is ensured to cut the submucosa S, and applying tension to the submucosa S becomes easier. Therefore, the procedure becomes easier. The other operations of the treatment tool 41 for an endoscope according to the present embodiment are the same as those of the above-described first embodiment.

Sixth Embodiment

Figure 30:
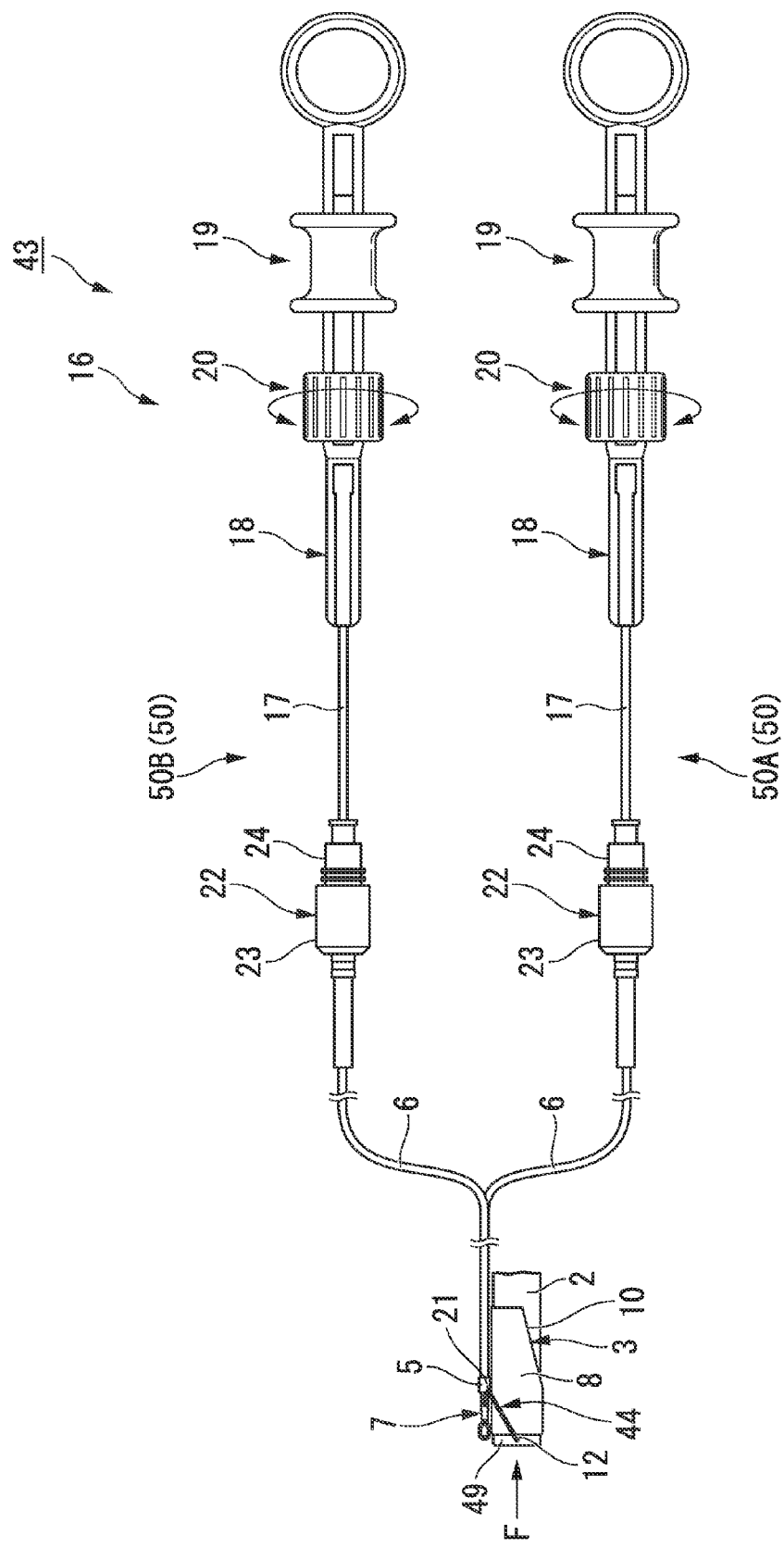
FIG. 30 is a front view schematically showing a state in which a treatment tool for an endoscope according to a sixth embodiment of the present invention is mounted on an endoscope.
Figure 31:
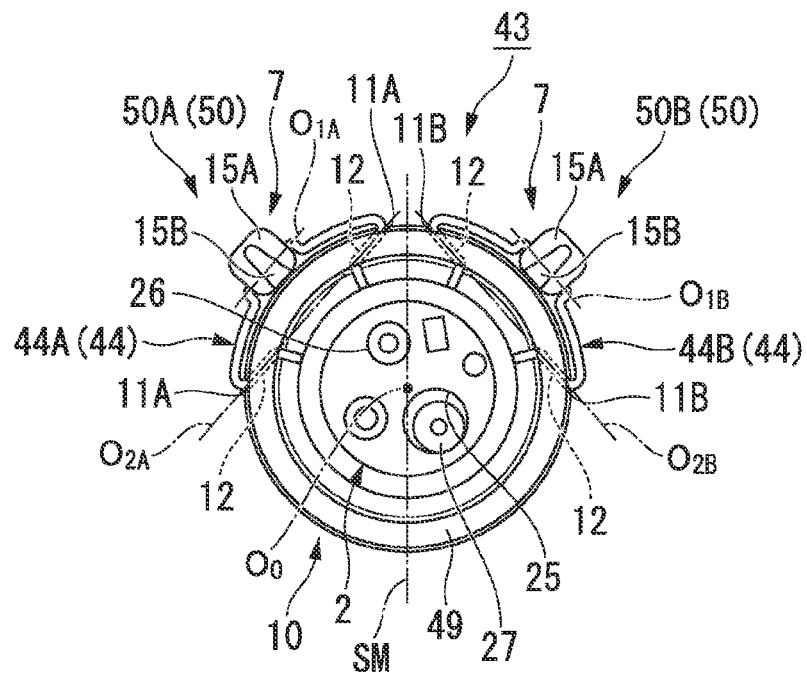
FIG. 31 is a view seen from the arrow F in FIG. 30.
Figure 32:
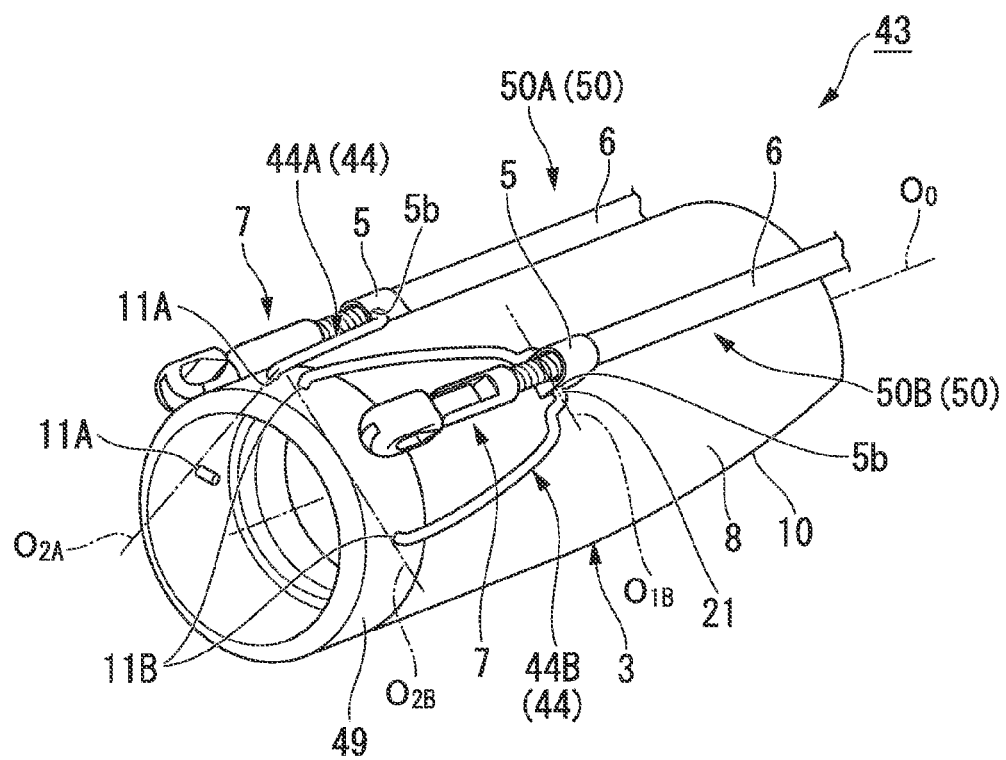
FIG. 32 is a perspective view schematically showing a distal end member and a treatment part of the treatment tool for an endoscope according to the sixth embodiment of the present invention.

A treatment tool for an endoscope according to the sixth embodiment of the present invention will be described. FIG. 30 is a front view schematically showing a state in which the treatment tool for an endoscope according to the sixth embodiment of the present invention is mounted on an endoscope. FIG. 31 is a view seen from the arrow F in FIG. 30. FIG. 32 is a perspective view schematically showing a distal end member and a treatment part of the treatment tool for an endoscope according to the sixth embodiment of the present invention.

As shown in FIG. 30, a treatment tool 43 for an endoscope according to the present embodiment includes a cap 49 and a plurality of connecting members 44 in place of the cap 9 and the connecting member 4 of the treatment tool 1 for an endoscope according to the first embodiment, and further includes the treatment tool main body 50 composed of the capturing part 7, the support member 14, the sheath 17, the tube 6, the second lock mechanism 22, and the operating part 16 equal in number to the connecting member 44. The connecting member 44 and the treatment tool main body 50 should both number two or more. In the present embodiment, as one example, the number of connecting members 44 is two, the connecting members 44A and 44B, and the number of treatment tool main bodies 50 is two, the treatment tool main bodies 50A and 50B. Hereinafter, descriptions will be provided focusing on content different from that of the first embodiment.

As shown in FIG. 31, the cap 49 includes the pair of holes 11A and the pair of holes 11B in place of the pair of holes 11 of the cap 9 according to the first embodiment. The pairs of holes 11A and 11B are through-holes that allow two points in a circumferential direction of the cap 49 to communicate with each other within a plane (paper plane of FIG. 31) perpendicular to the central axis $O_0$ of the distal end member 3. Therefore, an axis $O_{2A}$ ($O_{2B}$), which is a central axis of the pair of holes 11A (11B), is perpendicular to a position that is twisted from the central axis $O_0$ of the distal end member 3. In the present embodiment, the pairs of holes 11A and 11B are arranged to be shifted from a direction in which the slit 10 is open in a circumferential direction of the cap 49, and are provided at positions that are plane-symmetric to each other with respect to a center line SM of the slit 10 that passes through the central axis $O_0$. Therefore, the side surface of the mounting part 8 is positioned in a region between the pair of holes 11A (11B) without facing the slit 10 in an axial direction.

The connecting member 44A (44B) has the same configuration as the connecting member 4 according to the first embodiment except that the second pivot 12 of the connecting member 4 according to the first embodiment has a shape that is changed to be pivotally inserted into the pair of holes 11A (11B). Therefore, in the connecting member 44A (44B), the first pivot 21 is inserted into the through-hole 5b of the moving member 5 along an axis $O_{1A}$ ($O_{1B}$) parallel to the axis $O_{2A}$ ($O_{2B}$) and pivotally coupled to the moving member 5. In addition, in the connecting member 44A (44B), the second pivot 12 is inserted into the pair of holes 11A (11B) of the cap 49 and pivotally coupled to the distal end member 3. Therefore, the first pivot 21 in the connecting member 44A (44B) is pivotable about the axis $O_{2A}$ ($O_{2B}$) by the pair of holes 11A (11B).

According to the treatment tool 43 for an endoscope having such a configuration, the two treatment tool main bodies 50A and 50B are independently rotatably coupled to the distal end member 3.

Figure 33:
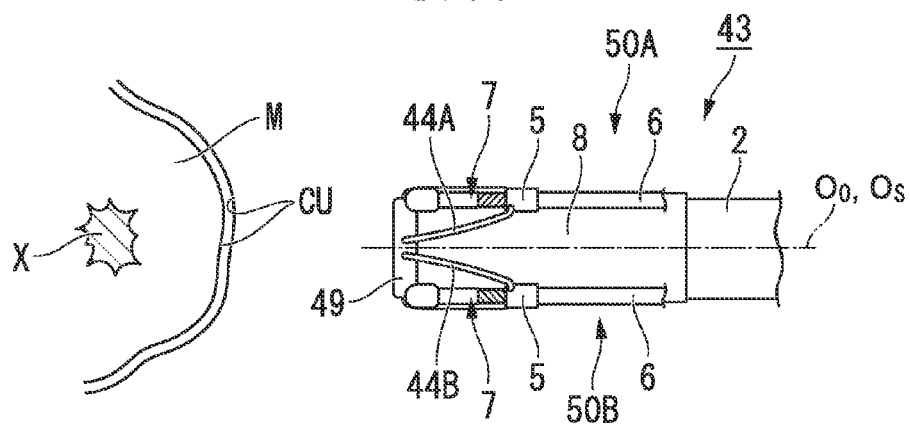
FIG. 33 is an explanatory diagram showing an operation of the treatment tool for an endoscope according to the sixth embodiment of the present invention.
Figure 34:
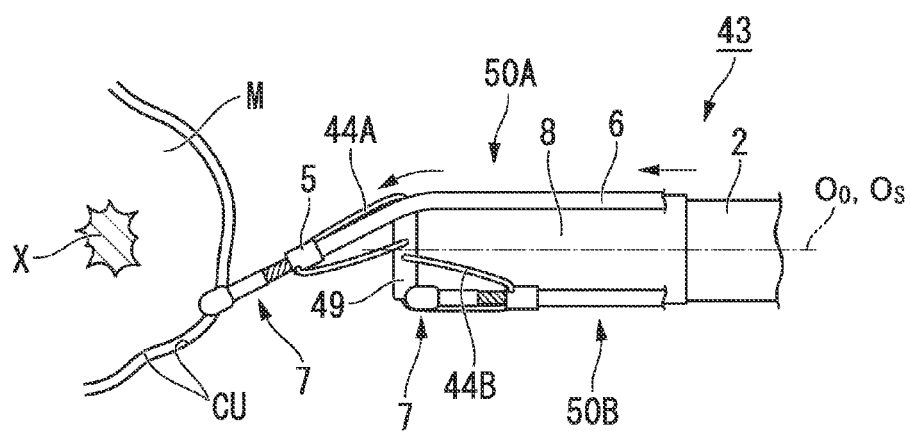
FIG. 34 is an explanatory diagram showing an example of an operation conducted after the operation shown in FIG. 33.
Figure 35:
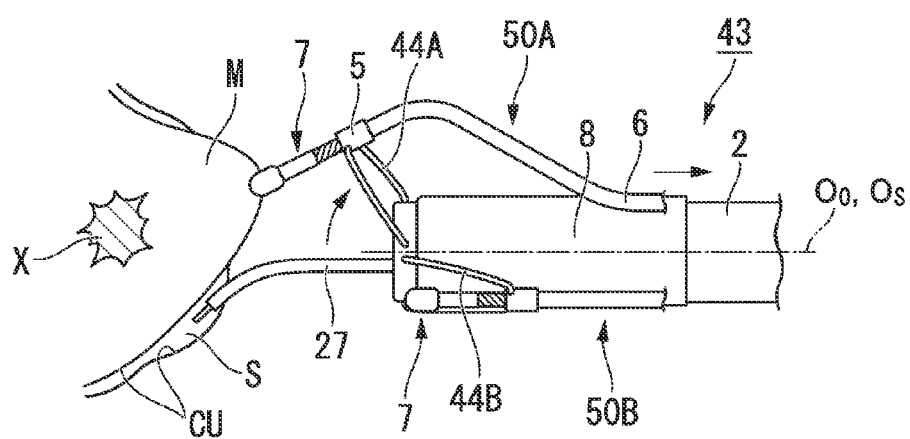
FIG. 35 is an explanatory diagram showing an operation conducted after the operation shown in FIG. 34.
Figure 36:
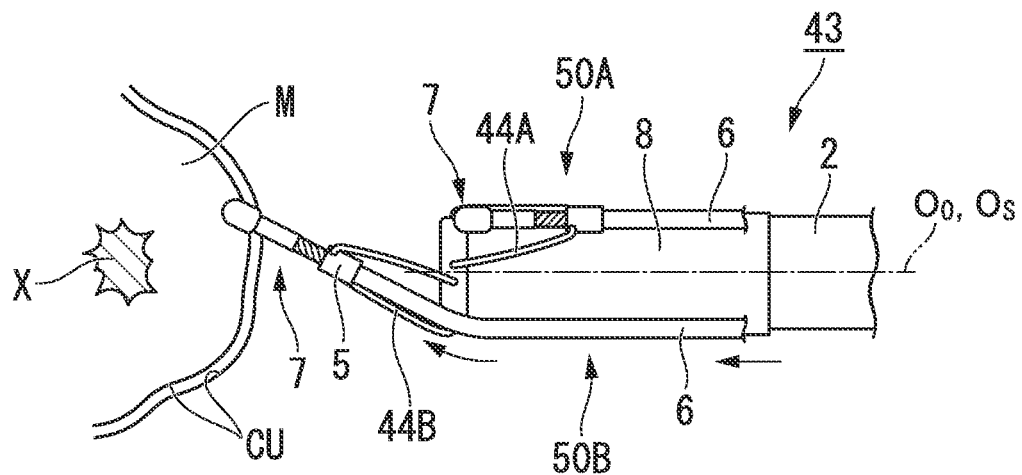
FIG. 36 is an explanatory diagram showing another example of an operation conducted after the operation shown in FIG. 33.
Figure 37:
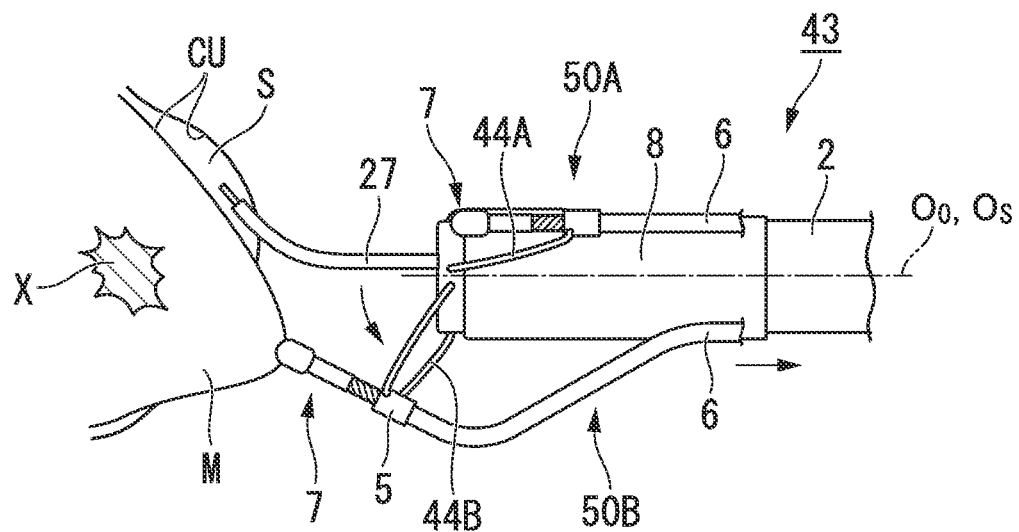
FIG. 37 is an explanatory diagram showing an operation conducted after the operation shown in FIG. 36.

Next, operations of the treatment tool 43 for an endoscope according to the present embodiment will be described. FIG. 33 is an explanatory diagram showing an operation of the treatment tool for an endoscope according to the sixth embodiment of the present invention. FIG. 34 is an explanatory diagram showing an example of the operation conducted after the operation shown in FIG. 33. FIG. 35 is an explanatory diagram showing an operation conducted after the operation shown in FIG. 34. FIG. 36 is an explanatory diagram showing another example of the operation conducted after the operation shown in FIG. 33. FIG. 37 is an explanatory diagram showing an operation conducted after the operation shown in FIG. 36.

According to the treatment tool 43 for an endoscope, when the two connecting members 44A and 44B independently rotate, it is possible to independently move the tubes 6 and the capturing parts 7 in the treatment tool main bodies 50A and 50B. Here, individual operations of the tubes 6 and the capturing parts 7 are the same as those of the first embodiment.

First, as shown in FIG. 33, while the capturing parts 7 of the treatment tool main bodies 50A and 50B are arranged in respective accommodating positions, the endoscope 2 and the treatment tool 43 for an endoscope are inserted near the lesion part X. Next, similar to the first embodiment, the cut end CU is formed around the lesion part X in front of the endoscope 2.

Next, as shown in FIG. 34, by moving the treatment tool main body 50A to the distal end side, the connecting member 44A rotates, the capturing part 7 of the treatment tool main body 50A is positioned near the cut end CU, and thus the cut end CU is grasped. In this case, when the connecting member 44A rotates, since the capturing part 7 is moved to intersect the central axis $O_S$ of the endoscope 2 in front of the endoscope 2 seen in a plan view, the cut end CU at the front side of the treatment tool main body 50B is grasped. In this state, when the treatment tool main body 50A is moved to the proximal end side, as shown in FIG. 35, the connecting member 44A rotates to the proximal end side, and the cut end CU is pulled upward. Therefore, the submucosa S below the cut end CU grasped by the capturing part 7 is lifted up and exposed in front of the endoscope 2. Also, the high frequency knife 27 is drawn from the endoscope 2, the submucosa S is pulled while a current is applied, and thus the submucosa S is cut and dissected.

In addition, when the submucosa S of the opposite side with the central axis $O_S$ interposed therebetween is cut and dissected, as shown in FIGS. 36 and 37, the connecting member 44B rotates and the cut end CU is grasped by the capturing part 7 of the treatment tool main body 50B. Therefore, similar to the above, the submucosa S can be lifted up and cut and dissected.

According to the treatment tool 43 for an endoscope, since the two capturing parts 7 can independently move to grasp sides of biological tissues, when the submucosa S at a side is cut and dissected, it is possible to ensure a sufficient field of view to cut the submucosa S at the side, and it is possible to apply appropriate tension to the submucosa S. Accordingly, the procedure becomes easier.

Also, while the above embodiments and modified examples have been described as examples in which the treatment part of the treatment tool for an endoscope is formed from the capturing part 7, the treatment part is not limited to the forceps that performs only grasping such as the capturing part 7. For example, the capturing part 7 may be configured so as to apply a high frequency current. In this case, a terminal configured to connect high frequency power and the operation wire is provided in the slider 19. The sheath 17 is covered with an insulating tube. According to the capturing part 7 modified in this manner, a hole can be made in tissues to create a starting point of incision, or hemostasis can be possible when there is bleeding. In addition, the treatment part is not limited to a type including the pair of openable and closable forceps members such as the capturing part 7, but other configurations such as a snare can be applied to the treatment part. In addition, as long as treatment is performed on biological tissues by the treatment part, the treatment part is not limited to a part grasping biological tissues. For example, a needle, a suturing instrument, or the like can be applied to the treatment part.

While the above embodiments and modified examples have been described as examples in which the treatment tool for an endoscope is used for a procedure of resecting the lesion part X occurring in the mucosa M, applications of the treatment tool for an endoscope are not limited to such a procedure. Each treatment tool for an endoscope can be used for other procedures.

While the second embodiment has been described as an example in which the external tube 30 is fixed to the mounting part 8, the external tube 30 is not necessarily fixed to the mounting part 8. For example, the external tube 30 can be fixed to the endoscope 2 by a band or the like.

While the fifth embodiment has been described as an example in which the two capturing parts 7 form the same treatment part, the treatment tool main bodies 50A and 50B can have different treatment parts.

In descriptions of the fifth embodiment, the distal ends of the two tubes 6 are bound by the moving member 42. However, in at least a range parallel with an insertion part of the endoscope 2, one tube having two juxtaposed lumens can be used in place of the two tubes 6.

While the fifth and sixth embodiments have been described as examples in which the two treatment tool main bodies 50A and 50B include the sheath 17, the moving member 5, the connecting member 44, and the tube 6 of the same configuration, these parts can have different configurations.

While exemplary embodiments of the present invention have been described above, the present invention is not limited to these embodiments. Additions, omissions, substitutions, and other modifications of the configuration can be made without departing from the spirit and scope of the present invention. The present invention is not limited to the above descriptions, and is only limited by the scope of appended claims.

Further, the present invention includes the following technical concepts.

(Note 1)

A treatment tool for an endoscope includes: a distal end member that is attached to a distal end of an endoscope and has a cylindrical shape; a treatment part performing treatment on biological tissues; an insertion part that is arranged so as to advance and retrace in an axis direction of the endoscope and has a distal end to which the treatment part is fixed; a connecting member rotatably connecting the treatment part and the distal end member; a first pivot pivotally coupling the connecting member and the treatment part; and a second pivot pivotally coupling the connecting member and the distal end member, wherein the connecting member has a movement area in which the treatment part is movable on the connecting member along the first pivot, and the second pivot is provided at a position at which the connecting member is capable of rotating such that the first pivot is moved to a position at a distal end side relative to the second pivot.

The object of the invention according to Note 1 is to avoid moving the treatment part that has grasped tissues when a cutting tool is moved by a bending manipulation of the endoscope and cutting and dissecting are performed. In the invention according to Note 1, even when the bending manipulation of the endoscope is performed, since the treatment part moves in a movement area of the connecting member, the treatment part that has grasped tissues does not move together with the endoscope.

What is claimed is:

1. A treatment tool for an endoscope comprising:
a distal end member that is attached to a distal end of an endoscope and has a cylindrical shape;
a tube that is arranged substantially parallel to an axis of the distal end member, and is arranged at a side surface of the distal end member;
a connecting member that includes
a first pivot part which has a first central axis extending in a direction intersecting an axis of the tube and which is coupled with the tube,
a second pivot part which has a second central axis substantially parallel to the first central axis of the first pivot part and which is coupled with the distal end member such that the second pivot part is capable of rotating about the second central axis relative to the distal end member; and a part that connects the first pivot part and the second pivot part; and a moving member that is fixed to a distal end of the tube and includes a through-hole through which the first pivot part is inserted;

wherein the second pivot part is coupled with the distal end member such that the first pivot part is capable of rotating about the second central axis of the second pivot part, and the moving member is freely movable in a longitudinal direction along the first central axis of the first pivot part.

2. The treatment tool according to claim 1, further comprising:

a treatment part that performs treatment on biological tissues; and an insertion part that has a distal end to which the treatment part is fixed, wherein the tube is configured to hold the insertion part such that the insertion part is capable of advancing and retracting.

3. The treatment tool according to claim 1, wherein the distal end member includes:

a mounting member configured to be detachably attached to the distal end of the endoscope; and a cap positioned at a distal end side of the mounting member.

4. The treatment tool according to claim 1, wherein the distal end member is provided with a coating part into which the tube is inserted in an advanceable and retractable manner.

5. The treatment tool according to claim 1, further comprising:

a treatment part that performs treatment on biological tissues; and an insertion part that has a distal end to which the treatment part is fixed, wherein the tube and the treatment part are configured to be prevented from rotating relative to each other.

* * * * *